(12) United States Patent
Lane et al.

(10) Patent No.: US 6,239,171 B1
(45) Date of Patent: *May 29, 2001

(54) TOCOTRIENOLS AND TOCOTRIENOL-LIKE COMPOUNDS AND METHODS FOR THEIR USE

(75) Inventors: Ronald H. Lane, Phoenix, AZ (US);
Asaf A. Qureshi, Madison, WI (US);
Winston A. Salser, Pacific Palisades, CA (US)

(73) Assignee: Lipogenics, Inc., Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/182,530

(22) Filed: Oct. 28, 1998

Related U.S. Application Data

(62) Continuation of application No. 08/991,912, filed on Dec. 16, 1997, now Pat. No. 5,919,818, which is a continuation of application No. 08/719,284, filed on Sep. 24, 1996, now Pat. No. 5,821,264, which is a continuation of application No. 08/244,215, filed as application No. PCT/US92/10277 on Nov. 20, 1992, which is a continuation-in-part of application No. 07/796,486, filed on Nov. 22, 1991, now abandoned.

(51) Int. Cl.[7] ................. A61K 31/355; C07D 311/22; C07D 311/72
(52) U.S. Cl. .................. 514/458; 514/456; 549/398; 549/401; 549/404; 549/405; 549/408; 549/409
(58) Field of Search ................. 549/398, 401, 549/404, 405, 408, 409; 514/456, 458

(56) References Cited

U.S. PATENT DOCUMENTS

| | | | |
|---|---|---|---|
| 3,064,012 | 11/1962 | Folkers et al. | 260/345.5 |
| 3,122,565 | 2/1964 | Kijima et al. | 549/413 |
| 4,603,143 | 7/1986 | Schmidt | 514/458 |
| 4,788,304 | 11/1988 | Marshall et al. | 549/549 |
| 5,034,420 | 7/1991 | Wang | 514/680 |
| 5,138,075 | 8/1992 | Ohgaki et al. | 549/413 |
| 5,204,373 | 4/1993 | Pearce | 514/720 |
| 5,217,992 | 6/1993 | Wright et al. | 514/458 |
| 5,296,508 | 3/1994 | Pearce | 514/510 |
| 5,348,974 | 9/1994 | Wright et al. | 514/456 |
| 5,393,776 | 2/1995 | Pearce | 514/486 |
| 5,591,772 | * 1/1997 | Lane et al. | 514/458 |
| 5,821,264 | * 10/1998 | Lane et al. | 514/458 |
| 5,919,818 | * 7/1999 | Lane et al. | 514/458 |

FOREIGN PATENT DOCUMENTS

| | | |
|---|---|---|
| 3221506 | 12/1983 | (DE) . |
| 304842 | 3/1989 | (EP) . |
| 421419 | 4/1991 | (EP) . |
| 870638 | 6/1961 | (GB) . |
| 1011319 | 11/1966 | (GB) . |
| 1506076 | 4/1978 | (GB) . |
| 2-264712 | 10/1990 | (JP) . |

OTHER PUBLICATIONS

Qureshi et al., *Journal of Biological Chemistry* vol. 261, No. 23 (1986) pp. 10544–10550.
Schudel et al., *Helvetica Chimica Acta* vol. 46, No. 7 (1963) 2517–2526.
Patent Abstracts of Japan, vol. 9, No. 91 (C–277)(1814) Apr. 19, 1958 of JP,A, 59 222 414 (Kuraray) Dec. 12, 1984.

* cited by examiner

*Primary Examiner*—Richard L. Raymond
(74) *Attorney, Agent, or Firm*—Lyon & Lyon LLP

(57) ABSTRACT

The present invention relates to novel tocotrienols and tocotrienol-like compounds displaying biological activity. The tocotrienols and tocotrienol-like compounds of this invention may be conveniently obtained from biological sources or by chemical synthesis and may be used in pharmaceutical compositions, foodstuffs and dietary supplements. This invention also relates to the use of tocotrienols, tocotrienol-like compounds, and mixtures thereof, as hypocholesterolemic, antithrombotic, antioxidizing, antiathermogenic, antiinflammatory and immunoregulatory agents, or as agents useful to decrease lipoprotein (a) concentration in the blood or to increase feed conversion efficiency.

14 Claims, No Drawings

TOCOTRIENOLS AND TOCOTRIENOL-LIKE COMPOUNDS AND METHODS FOR THEIR USE

This application is a continuation of application Ser. No. 08/991,912, filed Dec. 16, 1997, now U.S. Pat. No. 5,919,818, which is a continuation of application Ser. No. 08/719,284, filed Sep. 24, 1996, now U.S. Pat. No. 5,821,264, which is a continuation of application Ser. No. 08/244,215, filed Aug. 15, 1994, now U.S. Pat. No. 5,591,772, which is a 371 of PCT/US92/10277, filed Nov. 20, 1992, which is a continuation-in-part of application Ser. No. 07/796,486, filed Nov. 22, 1991, now abandoned.

TECHNICAL FIELD OF THE INVENTION

The present invention relates to novel tocotrienols and tocotrienol-like compounds displaying biological activity. The tocotrienols and tocotrienol-like compounds of this invention may be conveniently obtained from biological sources or by chemical synthesis and may be used in pharmaceutical compositions, foodstuffs and dietary supplements. This invention also relates to the use of tocotrienols, tocotrienol-like compounds, and mixtures thereof, as hypocholesterolemic, antithrombotic, antioxidizing, antiatherogenic, antiinflammatory and immunoregulatory agents, or as agents useful to decrease lipoprotein (a) concentration in the blood or to increase feed conversion efficiency.

BACKGROUND OF THE INVENTION

Plant constituents have been proven useful in the prevention and treatment of a wide variety of diseases and conditions. For example, barley has been shown to be particularly effective in lowering lipid levels in animal models (A. A. Qureshi et al., "Suppression", *Lipids*, 20, pp. 814–24 (1985)). More specifically, α-tocotrienol, a chromanol isolated from barley extract, has been identified as a therapeutic agent for hypercholesterolemia (A. A. Qureshi et al., "The Structure Of An Inhibitor Of Cholesterol Biosynthesis isolated From Barley", *J. Biol. Chem.*, 261, pp. 10544–50 (1986)). In addition, tocotrienol, γ-tocotrienol and δ-tocotrienol have also been shown to reduce hypercholesterolemia in mammals (European patent application 421, 419).

Hypercholesterolemia involves high serum cholesterol levels and is a causative agent of diseases including arteriosclerosis, atherosclerosis, cardiovascular disease and xanthomatosis. In addition, high serum cholesterol levels are seen in patients suffering from diseases including diabetes mellitus, familial hypercholesterolemia, acute intermittent prothyria, anorexia nervosa, nephrotic syndrome, primary cirrhosis and various liver disorders, such as hepatitis and obstructive jaundice. Improvement of lipoprotein profiles and a decrease in total serum and low density lipoprotein cholesterol have been shown to retard the progression of such diseases, as well as to induce regression of clinically significant lesions in hypercholesterolemic patients.

Although the relationship between hypercholesterolemia and its many associated diseases, most notably cardiovascular disease, has been extensively studied, no clear answer to this worldwide problem has yet been found. As a result, coronary artery disease remains the leading cause of death in the United States and other developed countries. Coronary artery disease is the result of complex interactions between a large number of different processes, including lipoprotein metabolism, aggregation of blood platelets, blood coagulation and fibrinolysis. Accordingly, the cardiovascular risk profile of a given patient is dependent on these interactions.

In addition to lowering cholesterol levels, the cardiovascular risk profile of a patient may also be reduced by decreasing the levels of other factors in the serum and the blood. For example, reduction of thromboxane $A_2$ generation (measured by the levels of thromboxane $B_2$, a stable metabolite of thromboxane $A_2$) and platelet factor 4 levels in the serum lessens the risk of cardiovascular disease because of decreased thrombogenic activity.

Thromboxane $A_2$ and platelet factor 4 levels are also associated with other biological activities. For example, when reduction of these factors is accompanied by a reduction in macrophage cell count, lower tumor necrosis factor (TNF) levels and lower arachidonic acid levels in bodily tissues, reduced levels of prostaglandins, leukotrienes and interleukins are implicated. Reduction of these factors, therefore, leads to a decrease in the inflammation accompanying a wide variety of diseases. In addition, since prostaglandins inhibit glucose-induced insulin release and increase glucagon secretion, an increased insulin to glucagon ratio may also result from the reduction in prostaglandins. Such an increase is useful in improving glucose intolerance in diabetes mellitus and restoration of acute glucose-induced insulin response in non-insulin-dependent diabetes mellitus.

It has been noted that there is a low incidence of cardiovascular disease in populations consuming large amounts of cereal grains. Soluble and insoluble fibers have, in the past, been viewed as the agents responsible for cholesterol reduction in such populations (see D. Kritchevsky et al., "Fiber Hypercholesterolemia and Atherosclerosis", *Lipids*, 13, pp. 366–69 (1978)). Recently, the hypocholesterolemic effects of cereal grains have been attributed to natural components of the grains—tocotrienols ("$T_3$") and structurally similar compounds, such as tocopherols ("T"). Tocotrienols and tocopherols occur naturally in small quantities in a wide variety of plant sources, such as rice bran, palm oil and barley (A. A. Qureshi et al., "Lowering of Serum Cholesterol in Hypercholesterolemic Humans by Tocotrienols (Palmvitee)", *Am. J. Clin. Nutr.*, 53, pp. 1021S–6S (1991)).

As a class, the tocopherols, including d-α-tocopherol (vitamin E), have been extensively studied. As a result of these studies, certain biological activities have been attributed to the tocopherols. Such activities include platelet aggregation and antioxidant functions (see, for example, E. Niki et al., "Inhibition of Oxidation of Biomembranes By Tocopherol", *Annals of the New York Academy of Sciences*, 570, pp. 23–31 (1989) and K. Fukuzawa et al., "Increased Platelet-Activating Factor (PAF) Synthesis in Polymorphonuclear Leukocytes of Vitamin E-Deficient Rats", *Annals of the New York Academy of Sciences*, 570, pp. 449–453 (1989)). Although the exact structure-function relationship is not known, several experiments have highlighted the importance of the phytyl side chain in the biological activity of tocopherols (see W. A. Skinner et al., "Antioxidant Properties of α-Tocopherol Derivatives and Relationships of Antioxidant Activity to Biological Activity", *Lipids*, 5(2), pp. 184–186 (1969) and A. T. Diplock, "Relationship of Tocopherol Structure to Biological Activity, Tissue Uptake, and Prostaglandin Biosynthesis", *Annals of the New York Academy of Sciences*, 570, pp. 73–84 (1989)).

In contrast to the tocopherols, interest in the tocotrienols has been limited, as those compounds were not typically considered to be biologically useful. Recently, however, studies have indicated that tocotrienols may be biologically active. For example, U.S. Pat. No. 4,603,142 identifies d-α-tocotrienol, isolated from barley extracts, as an inhibitor of cholesterol biosynthesis. See also A. A. Qureshi et al. (1986), supra. Various human and animal studies have confirmed the impact of pure tocotrienols, isolated from barley, oats and palm oil, on cholesterol biosynthesis, specifically LDL-cholesterol (A. A. Qureshi et al., "Dietary Tocotrienols Reduce Concentrations of Plasma Cholesterol, Apolipoprotein B, Thromboxane $B_2$ and Platelet Factor 4 In Pigs With Inherited Hyperlipidemias", Am. J. Clin. Nutr., pp. 1042S–46S (1991); A. A. Qureshi et al., "Lowering Of Serum Cholesterol In Hypercholesterolemic Humans By Tocotrienols (Palmvitee)", Am. J. Clin. Nutr., 53, pp. 1021S–26S (1991); D. T. S. Tan et al., "The Effect Of Palm Oil Vitamin E Concentrate On The Serum And Lipoprotein Lipids In Humans", Am. J. Clin. Nutr., 53, pp. 1027S–30S (1991)). In addition, tocotrienol, γ- and δ-tocotrienol have been indicated for use in the treatment of hypercholesterolemia, hyperlipidemia and thromboembolic disorders (European patent application 421,419).

The five known naturally occurring tocotrienols have been designated tocotrienol, α-, β-, γ- and δ-tocotrienol. Those compounds exhibit varying degrees of hypercholesterolemic activity and have also been used as antithrombotic agents and antioxidants. α-$T_3$, for example, displays antioxidant activity against lipid peroxidation in rat liver microsomal membranes and against oxidative damage of cytochrome P-450 (E. Serbinova, *Free Radical Biology and Medicine*, in press (1991)). Despite these activities, the known tocotrienols have not found wide-spread therapeutic use.

Accordingly, the need still exists for compounds which, as single agents, can safely and effectively act as hypercholesterolemic, antithrombotic, antioxidizing, antiatherogenic, antiinflammatory and immunoregulatory agents.

SUMMARY OF THE INVENTION

The present invention solves the problems referred to above by providing novel tocotrienols, tocotrienol-like compounds, and mixtures thereof, that are useful as hypocholesterolemic, antithrombotic, antioxidizing, antiatherognic, antiinflammatory and immunoregulatory agents. These novel tocotrienols and tocotrienol-like compounds are also useful in decreasing lipoprotein (a) ("Lp(a)") concentration in the blood, increasing feed conversion efficiency, and in the treatment or prevention of conditions such as fever, edema, diabetes mellitus, cancer, signs of aging, pain, rheumatoid diseases, septic shock, chronic fatigue syndrome and functio laesa.

The novel tocotrienols and tocotrienol-like compounds of the present invention are useful in inhibiting the synthesis of HMG-CoA reductase, reducing lipogenesis and increasing the HDL/LDL cholesterol ratio, as well as reducing total serum cholesterol, low density lipoprotein-cholesterol, Lp(a), apolipoprotein B, thromboxane $A_2$, platelet factor 4, triglycerides and glucose. Because of such individual activities, these compounds are useful in treating diseases, for example, coronary artery disease, which result from the interaction of processes such as lipoprotein metabolism, aggregation of blood platelets, blood coagulation and fibrinolysis. Accordingly, the compounds of this invention are useful to improve the overall cardiovascular profile of patients.

This invention also provides novel uses for the known tocotrienols as antiinflammatory and immunoregulatory agents, to decrease Lp(a) concentration in the blood, to increase feed conversion efficiency, and for the treatment or prevention of conditions such as fever, edema, diabetes mellitus, pain, septic shock, chronic fatigue syndrome and functio laesa.

Advantageously, the tocotrienol and tocotrienol-like compounds reduce serum TNF and IL-1 levels. These activities render the compounds useful in reducing active and chronic inflammation, such as that associated with rheumatoid disease. Also, such activities render the compounds useful in treating, preventing or lessening the severity of immunoregulatory diseases, such as autoimmune diseases, and in preventing or treating pain, septic shock, chronic fatigue syndrome, functio laesa and oxidative conditions.

The effects of tocotrienol and tocotrienol-like compounds on lipid metabolism also influence the regulation of antibody production. Thus, these compounds are useful in modulating immune function through adjustments in fatty acid levels.

Tocotrienol and tocotrienol-like compounds also decrease glucose levels by mediating the levels of insulin and glucagon. By increasing the insulin to glucagon ratio in the blood, these compounds are useful in increasing glucose intolerance in diabetes mellitus and restoring acute glucose-induced insulin response in non-insulin dependent diabetes mellitus patients.

The novel tocotrienols and tocotrienol-like compounds of this invention are characterized by specific structural characteristics and specific biological activity or, alternatively, by specific high performance liquid chromatography ("HPLC") elution profiles and specific biological activity. More particularly, the compounds of this invention may be characterized by three structural features: (1) a hydrogen donor group (or a group which can be hydrolyzed to a hydrogen donor group) attached to an aromatic ring system, (2) an atom having at least one lone pair of electrons, said electrons being in conjugation with the aromatic system and (3) a side chain comprising one or more isoprenoid or isoprenoid-like units attached to a position adjacent to that atom. This invention also encompasses the hydrolysis and oxidation products obtained from such compounds. In addition, the compounds of this invention having the above-mentioned structural characteristics are also characterized by the ability to inhibit the activity of β-hydroxy-β-methyl glutaryl coenzyme A (HMG-CoA) reductase. Furthermore, these compounds are effective in the treatment or prevention of one or more of the following diseases or conditions: hypercholesterolemic diseases, thrombotic disease, oxidative conditions, inflammation or immunoregulatory diseases or, alternatively, in increasing feed conversion efficiency.

According to the alternate embodiment, the novel tocotrienols and tocotrienol-like compounds of this invention may be characterized by an elution time of at least 22 minutes under the following HPLC conditions: μ-Porasil column (Waters column, 10μ, 4 mm×30 cm) using an isocratic system of hexane and isopropanol (99.75%:0.25%, v/v) at a flow rate of 1.3 ml/min. The particular compound is detected at an exitation wavelength of 295 nm and an emission wavelength of 330 nm (fluorescence detector) and UV absorption at 295 nm. In addition to the above-defined elution profile, the novel tocotrienols of this invention are also characterized by the ability to inhibit the activity of HMG-CoA reductase.

According to this invention, tocotrienols and tocotrienol-like compounds may be conveniently obtained from biological sources. Alternatively, they may be synthesized using conventional chemical methodologies. In a preferred embodiment of this invention, the tocotrienols and tocotrienol-like compounds are isolated and purified from stabilized biological sources. This invention also encompasses the techniques used to purify such compounds.

In a preferred embodiment of this invention, the tocotrienols, tocotrienol-like compounds and mixtures thereof, may be administered to an animal or a human as a pharmaceutical composition, a foodstuff or a dietary supplement, to treat or prevent hypercholesterolemic diseases, thrombotic diseases, oxidative or atherogenic conditions, inflammation or immunoregulatory diseases. Advantageously, these compositions, foodstuffs and dietary supplements may also be used to increase feed conversion efficiency, decrease Lp(a) concentration in the blood and in the treatment or prevention of fever, edema, diabetes mellitus, cancer, signs of aging, pain, rheumatoid diseases, septic shock, chronic fatigue syndrome and functio laesa.

DETAILED DESCRIPTION OF THE INVENTION

In order that the invention herein described may be more fully understood, the following detailed description is set forth. In the description, the following terms are employed:

Biological source—Any natural or recombinant plant source, natural or transgenic animal source, microbial source (e.g., bacteria), fungi, yeast, algae, higher plant source, or derivative thereof, which contains one or more tocopherol, tocotrienol or tocotrienol-like compounds.

Stabilization—A process effective to increase the recoverable amounts of tocopherols, tocotrienols and tocotrienol-like compounds in a biological source by one or a combination of: (1) inactivating enzymes which are capable of degrading tocotrienols and tocotrienol-like compounds in that biological source, (2) breaking bonds or otherwise interfering with the interactions—such as hydrogen bonds, covalent bonds, ionic bonds, Van der Waals forces, London forces and hydrophobic or hydrophilic interactions which bind the desired products to proteins, sugars, lipids, carbohydrates, glycoproteins, other biological molecules (i.e., amino acids or nucleotides) or other membrane components, or combinations thereof, in the biological source—which retain tocotrienols and tocotrienol-like compounds in that biological source, thus facilitating the release of those desired compounds, or (3) increasing the solubility of the tocotrienols and tocotrienol-like compounds of that biological source beyond that prior to stabilization or beyond the level of solubility of the tocotrienols of a corresponding non-stabilized biological source. As a result of stabilization, tocotrienols and tocotrienol-like compounds in a biological source may be recovered in higher yields than those realized from a corresponding non-stabilized biological source.

Tocol—A mixture of one or more compounds selected from tocotrienols (T), tocotrienols ($T_3$), and tocotrienol-like ($T_3$-like) compounds.

Tocotrienol-like—Any biologically active compound which is contained in or derived from a biological source and (1) which is released, or whose release is facilitated, upon stabilizing that source or (2) whose recoverable amount in that source is increased by stabilizing that source. Such tocotrienol-like compounds include any biologically active compound displaying the biological activity of a tocotrienol which inhibits the activity of HMG-CoA reductase as measured by an in vitro HMG-CoA reductase assay, such as that described in D. J. Shapiro et al., "Microassay for β-hydroxy-β-methyglutaryl-CoA Reductase in Rat Liver and in L-cell Fibroblasts", *Biochim. Biophys. Acta,* 370, p. 369 (1974). Tocotrienol-like compounds include, but are not limited to, any electron transfer ring compounds, antioxidant type compounds, redox compounds and compounds similar to or containing the three structural features that characterize the tocotrienols of this invention. Specific examples of $T_3$-like compounds are ubiquinones, plastoquinones, isoquinones, phylloquinones, benzoquinones, flavanols, flavanoids, coumarins, unsaturated terpenoids and unsaturated isoprenoids. The term "$T_3$-like compound" also encompasses analogues, homologs, isomers and derivatives of such compounds, such as prenylated derivatives or pyrolytic derivatives.

Preferred tocotrienol-like compounds have the following structures:

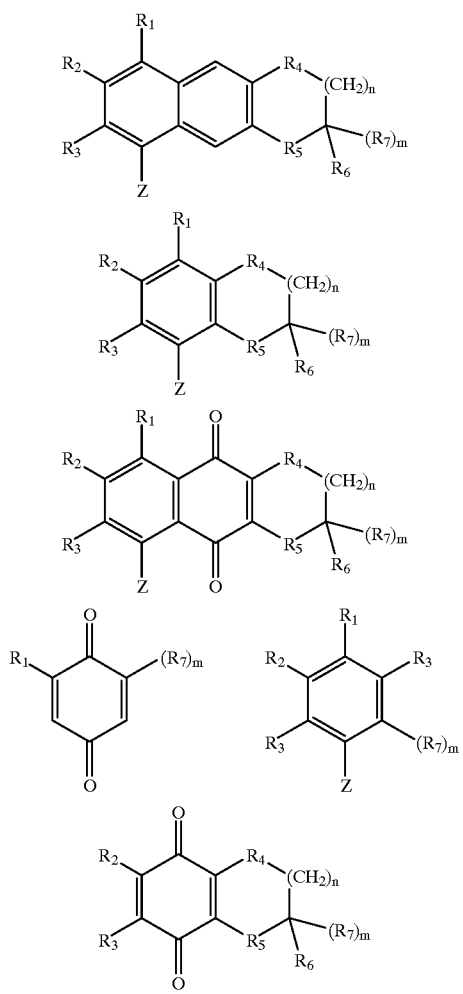

and salts, oxidation products and hydrolysis products thereof wherein:

$R_1$ and $R_3$ is each independently selected from the group consisting of H, halogen, OH, $OCH_3$ and $C_1$–$C_6$ branched or unbranched alkyls;

$R_2$ is selected from the group consisting of OH, $NHR_8$, $CO_2Y$, $C(R_8)_2CO_2H$, and $C_1$–$C_6$ branched or unbranched alkyls substituted by OH, $NHR_8$, $CO_2H$ or $C(R_8)_2CO_2H$;

$R_4$ is selected from the group consisting of O, NH, CH—$R_9$, C=O and CH—OH;

$R_5$ is selected from the group consisting of $CH_2$, CHOH, O, S and NH;

$R_6$ is selected from the group consisting of H and $C_1$–$C_6$ branched or unbranched alkyls;

Each $R_7$ independently represents

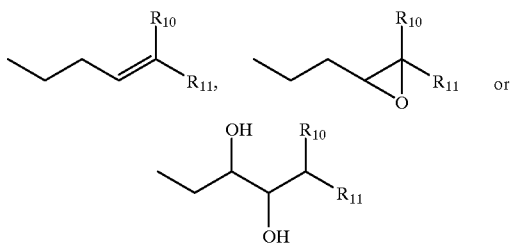

wherein $R_{10}$ is selected from the group consisting of H, $NH_2$ and $C_1$–$C_6$ branched or unbranched alkyls;

$R_8$ and $R_9$ is each independently selected from the group consisting of H and $C_1$–$C_6$ branched or unbranched alkyls;

Each $R_{11}$ is independently selected from the group consisting of H, $C_1$–$C_6$ branched or unbranched alkyls, $CH_2OH$, $CO_2H$ or OH;

Y is H or $C_1$–$C_{18}$ branched or unbranched alkyls, preferably $C_1$–$C_4$ alkyls;

Z is H, halogen, OH, $CH_2OH$, $CH_3$, $OCH_3$ or $COCH_3$;

n is an integer from 0–4; and m is an integer from 1–30, more preferably 1–20 or most preferably 3–10.

TRF—A tocotrienol-rich fraction obtained by the stabilization and extraction of a biological source. It typically contains varying amounts of the five known tocotrienols, the known tocopherols and the novel tocotrienols and tocotrienol-like compounds of this invention. Most commonly, the TRF will be composed of about 50% to about 90% tocotrienols and tocotrienol-like compounds. The TRF, may be used for any of the uses described herein for either the known tocotrienols or the novel tocotrienols and tocotrienol-like compounds of this invention.

TRF Standard—A tocotrienol-rich fraction (TRF) obtained from palm oil (A. A. Qureshi et al. (1991), supra). The TRF Standard contains varying amounts of α-, γ- and δ-tocotrienol and α-tocopherol but essentially none of the novel tocotrienol and tocotrienol-like compounds of this invention.

Enhanced—The state of a stabilized biological source, wherein the recoverable amount of the novel tocotrienols and tocotrienol-like compounds of this invention is increased beyond that recoverable from the biological source prior to stabilization.

Foodstuff—Substances that can be used or prepared for use as food for an animal or a human. Foodstuffs include substances that may be used in the preparation of food (such as frying oils) or food additives. For example, foodstuffs include animals used for human consumption or any product therefrom, such as, for example, eggs. Such animals themselves may have ingested or been treated with one or more tocotrienol or tocotrienol-like compound, or foodstuffs containing them. As discussed herein, after ingesting or being otherwise administered tocotrienols or tocotrienol-like compounds, such animals retain the advantages hypocholesterolemic, antithrombotic, antioxidizing, antiatherogenic, antiinflammatory and immunoregulatory properties of the tocotrienols and tocotrienol-like compounds.

HPLC elution time or profile—Except where otherwise noted, the term "HPLC elution time or profile" refers to the time necessary for a given compound to elute from the HPLC column or the characteristic profile of a mixture of compounds (20 µl) under the following conditions: µ-Porasil column (Waters column, 10µ, 4 mm×30 cm) using an isocratic system of hexane and isopropanol (99.75%L0.25%, v/v) at a flow rate of 1.3 ml/min. The compound is detected at an exitation wavelength of 295 nm and an emission wavelength of 330 nm (fluorescence detector) and UV absorption at 295 nm.

The individual tocotrienols and tocotrienol-like compounds of this invention constitute a novel class of biologically active compounds. Several of these compounds occur naturally in small quantities in biological sources. Therefore, in a preferred embodiment of this invention, tocotrienols and tocotrienol-like compounds are recovered from biological materials which have been stabilized and extracted according to the processes described in copending International patent application PCT/US91/03626, filed on May 23, 1991. The stabilization and recovery process disclosed therein enhances or increases the yields of tocotrienols and tocotrienol-like compounds recovered from biological sources.

The tocotrienol and tocotrienol-like compounds may be recovered from any biological materials including, but not limited to, oats, wheat, rye, barley, soybean, wheat germ, wheat bran, corn, rice (including whole kernel, husk or hull, endosperm and germ), cottonseed, milkweed, flax, sesame, rice bran, parboiled brown rice, brown rice flour, olives, vegetable oil distillant, fruit concentrate evaporate, barley bran, palm oil, wheat germ oil, rice bran oil, barley oil, coconut oil, cottonseed oil, soybean oil, other cereal grains and other cereal grain oils, plant tissues, flowers, bushes (such as juniper), trees (such as pine and rubber), fruits (such as melons, berries, tomatoes and citrus fruits), vegetables, grasses (such as alfalfa), fungi (such as mushrooms), leaves, seeds (such as sesame, millet and pine), such as sesame seeds and pine seeds, stems, bark, roots, nuts (such as cashews and almonds) and legumes (such as peanuts), or portions thereof. We have noted that the tocotrienols and tocotrienol-like compounds decompose in the biological source over time. Therefore, we prefer to use freshly harvested biological sources. Most preferably, the biological source is freshly harvested, stabilized rice bran.

Alternatively, the tocotrienols and tocotrienol-like compounds may be obtained from a non-stabilized source or synthesized according to known chemical methodology. Typical synthetic routes are described in J. W. Scott et al., "Synthesis of (2R, 4'R, 8'R)-α-Tocopherol and (2R, 3'E, 7'E)-α-Tocotrienol", Helv. Chem. Acta, 59, pp. 290–306 (1976) and P. Schudel et al., "Die Synthese von rac. all-trans δ- und ε-Tocopherol", Helv. Chem. Acta., 46, pp. 2517–2526 (1963). An alternative synthetic scheme is proposed in European patent application 421,419.

The tocotrienols and tocotrienol-like compounds of this invention may be altered by known chemical means to produce various derivatives or analogues. Such derivatives or analogues may be more easily isolated in pure form, or more resistant to degradation, or posses other desired characteristics. Such derivatives and analogues are also envisioned by this invention. Known chemical means to alter the compounds of this invention include, but are not limited to, heating in the presence or absence of air or in an inert or reactive gas environment (or in a mixture of inert and active gases) and pyrolysis.

This invention encompasses the d- or l-isomer and the d, l-racemic mixture of each tocotrienol and tocotrienol-like compound. However, the naturally occurring d-isomer is preferred. This invention also includes mixtures of at least one novel tocotrienol or tocotrienol-like compound of this invention with one or more of the known tocotrienols.

The tocotrienols and tocotrienol-like compounds of this invention may be characterized either by specific structural characteristics or alternatively, by a specific elution profile and specific biological activity. In the former case, the compounds of this invention share three structural features: (1) a hydrogen donor group (or a group which can be hydrolyzed to a hydrogen donor group) attached to an aromatic ring system, (2) an atom having at least one lone pair of electrons, said electrons being in conjugation with the aromatic system and (3) a side chain comprising one or more isoprenoid or isoprenoid-like units attached to a position adjacent to that atom. This invention also encompasses the hydrolysis and oxidation products obtained from such compounds. These compounds are effective in increasing feed conversion efficiency, decreasing Lp(a) concentration in the blood or, alternatively, in the treatment or prevention of one or more of the following diseases or conditions: immunoregulatory disease, inflammation, fever, edema, diabetes mellitus, cancer, signs of aging, pain, rheumatoid diseases, septic shock, chronic fatigue syndrome and functio laesa.

According to an alternate embodiment, the novel tocotrienols and tocotrienol-like compounds of this invention may be characterized by an elution time and specific biological activity. These compounds elute after at least 22 minutes under the following high performance liquid chromatography (HPLC) conditions: Porasil column (Waters column, 10μ, 4 mm×30 cm) using an isocratic system of hexane and isopropanol (99.75%:0.25%, v/v) at a flow rate of 1.3 ml/min. The compound if detected at an exitation wavelength of 295 nm and an emission wavelength of 330 nm (fluorescence detector) and UV absorption at 295 nm. In addition to the above-defined elution profile, the novel tocotrienols and tocotrienol-like compounds of this invention are also characterized by the ability to inhibit the activity of β-hydroxy-β-methyl glutaryl coenzyme A reductase ("HMG-CoA reductase").

The preferred class of compounds of this invention is of formula I:

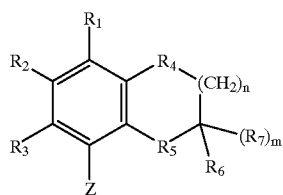

above. As herein described above, the compounds of formula I do not include desmethyl-tocotrienol (3,4-dihydro-2-methyl-2-(4,8,12-trimethyltrideca-3'(E),7'(E),11'-trienyl)-2H-1-benzopyran-6-ol).*

* The compounds of formula I also exclude α-, β-, γ- and 68-tocotrienol.

Typical hydrolysis products of the compounds of formula I which are also envisioned by this invention include, but are not limited to, compounds of formula II:

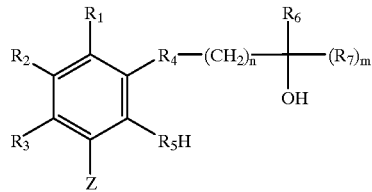

wherein $R_1$–$R_{10}$, Z, n and m are as defined as above. Preferred compounds are the compounds of formula I,
wherein $R_1$, $R_3$ and Z are each independently H, halogen, OH, $OCH_3$ or $CH_3$; R is OH, $OCH_3$ or $NH_2$; $R_4$ is C=O, $CH_2$ or NH; $R_5$ is O, S, $CH_2$ or NH; $R_6$ is H or $CH_3$; $R_{10}$ and $R_{11}$ are each independently H or $CH_3$; n is 0 or 1; and m is 3–10.

The most preferred compounds are the compounds of formula I, wherein $R_1$, $R_3$, Z, $R_8$ and $R_9$ are each hydrogen, $R_2$ is OH, $R_4$ is $CH_2$, $R_5$ is $CH_2$ or O, $R_6$ is H or $CH_3$, $R_{10}$ is H or $CH_3$, n is 1 and m is 3.

The novel compound, 3,4-dihydro-2-(4,8,12-trimethyltrideca-3'(E),7'(E),11'trienyl)-2H-1-benzopyran-6-ol ("$P_{25}$"), is representative of the class of compounds according to formula I. The structure of this compound is shown below:

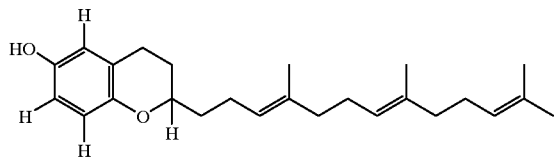

Tocotrienols and tocotrienol-like compounds of this invention having the above-defined structural features are also characterized by biological activity. They are useful in increasing feed conversion efficiency, decreasing Lp(a) concentration in the blood or in the treatment or prevention of one or more of the following diseases or conditions: immunoregulatory disease, inflammation, fever, edema, diabetes mellitus, cancer, signs of aging, pain, rheumatoid diseases, septic shock, chronic fatigue syndrome and functio laesa. They may also reduce the levels of TNF, IL-1 and IL-1 stimmulatory products including possibly IL-2, IL-6, IL-8, GMCSF, prostaglandins and gamma interferon, while increasing antibody titers in response to foreign proteins. By virtue of these activities, these compounds may result in a decrease in the release of superoxide and other cytotoxins produced by neutrophils, mast cells, basophils, monocyctes and macrophages, eosinophils, platelets, lumphocytes and polymorphonuclear leukocytes, endothelial tissue and other immunoregulatory tissues. These compounds may also effect an increase in antibody titers.

HMG-CoA reductase catalyzes the rate-limiting step of cholesterol biosynthesis. Therefore, a reduction in its activity decreases the total amount of cholesterol in the serum of animals and humans alone, or in combination with a low fat, low cholesterol diet. The effects are most noticeable in hypercholesterolemic individuals with poor dietary regimens. Typically, the tocotrienols and tocotrienol-like compounds of this invention reduce the activity of HMG-CoA reductase by at least about 15% in the in vitro assay described in Shapiro (supra), at a concentration of 10–20 μg/ml. More preferably, however, the HMG-CoA reductase activity is reduced by at least about 20% and most preferably by about 25%.

While not wishing to be bound by theory, we believe that some of the antiinflammatory, antioxidizing and immunoregulatory properties of the tocotrienol and tocotrienol-like compounds is a result of an inhibition in the production of free arachidonic acid.

We believe that the inhibition in the production of arachidonic acid is caused by either the inhibition of phospholipase $A_2$ or alternatively, by increasing the amount of corticosterone level in the blood. Phospholipase $A_2$ cleaves at C-2 of phosphate head groups, resulting in the release of free arachidonic acid. Arachidonic acid can then be converted into a variety of biologically important molecules, such as the prostaglandins and thromboxanes (via the cyclooxygenase pathway) and the leukotriences (via the lipoxygenase pathway). We believe that the hydrogen donor group of the tocotrienol and tocotrienol-like compounds bonds with the phosphate or phospholipid groups of biological membranes. In conjunction with the aromatic system, it also plays a role in radical scavenging. The isoprenoid tail may act to stabilize the membrane—possibly by forming weak bonds with the lipid side chains. In addition, by optionally replacing the tocotrienol methyl with other substituents (such as, for example, hydrogen) at position 2 on the chromanol ring, we are able to maximize the stabilization of the membrane. We believe that the aromatic system may also aid in tightening the surface of the membrane, thus increasing the steric hindrance for phospholipase $A_2$ and phospholipase C and decreasing its permeability. The aromatic system may also serve electron-transport and antioxidizing functions. Such a hypothesis would contribute to the explanation of the broad spectrum of biological functions that are effected by the administration of the tocotrienols and tocotrienol-like compounds according to this invention.

This invention also includes several novel uses for known tocotrienols, as well as tocotrienols and tocotrienol compounds as described herein. Examples include their use as antiinflammatory, antiatherogenic and immunoregulatory agents, for the treatment of fever, edema, diabetes melltius, cancer, signs of aging, pain, septic shock, chronic fatigue syndrome and functio laesa. In addition, tocotrienols and tocotrienol-like compounds are useful for increasing feed conversion efficiency—resulting in conversion of a greater percentage of food into protein rather than fat—and decreasing Lp(a) concentration in the blood. Known tocotrienols exhibit much of the same biological activity attributed to the novel tocotrienols and tocotrienol-like compounds of this invention. For example, known tocotrienols are capable of reducing total serum and LDL-cholesterol, apolipoprotein B, thromboxane $A_2$, platelet factor 4, triglycerides and glucose and inhibiting the activity of HMG-CoA reductase. They also reduce the levels of TNF and IL-1, and possibly IL-2 and gamma interferon, while increasing antibody titers in response to foreign proteins. In combination, these factors may produce a variety of advantageous and novel biological results, including a decrease in the release of superoxide and other cytotoxins produced by immunoregulatory cells and an increase in antibody titers.

Tocotrienols and tocotrienol-like compounds according to this invention are preferably recovered from stabilized biological sources. Alternatively, tocotrienols and tocotrienol-like compounds may be recovered from biological sources subjected to conventional food processing or preparation techniques. The stabilization process, however, greatly increases the recovered yields of these compounds. Without wishing to be bound by theory, we believe that a significant amount of tocotrienols and tocotrienol-like compounds are, in nature, bound to proteins or linked to phosphate or phospholipid groups in the membranes of biological sources. The significant increase in recovered amounts of these compounds realized by stabilization may be attributed to their release from protein or cleavage of phosphate or pyrophosphate moieties attached to the hydroxy group of the benzene ring in the tocotrienol or the hydrogen donor group of the tocotrienol-like compound. The application of heat and, optionally, pressure advantageously releases the compounds of this invention so that they may be recovered in good yield. Preferably, a combination of heat and pressure are used. Depending on the method of recovery used, the compounds of this invention may be extracted together with other components of the TRF.

We have found that microwaving is particularly effective to release membrane-bound $T_3$ and $T_3$-like compounds. We have also found that the following protocol maximizes the desired stabilization results: An amount (typically from 1 g to 1 kg) of a ground biological source (preferably rice or rice bran) is placed in a pyrex dish (typically, 10 cm—20 cm in diameter and 1.5 cm–15 cm in height). The dish can be covered or uncovered and optionally, a second dish containing a ground biological source can be stacked above the first. We prefer using one covered dish at a time. The biological source is then heated in a microwave oven at the maximum level (preferably 600–1500 watts) for 1–5 minute intervals, optionally in an ambient, vacuum or nitrogen blanket environment. Pressures of greater than 1 atmosphere may also optionally be used. After each heating interval, the sample should be stirred to homogeneity. The heating and stirring process is repeated 1–10 times. We prefer repeating the process 3–5 time for a 0.5 kg sample. The TRF may then be extracted, as described herein.

The TRF may be used directly, or it may be further separated in to its component compounds. It may be desired to isolate the novel tocotrienols and tocotrienol-like compounds from the TRF mixture.

The TRF typically contains varying degrees of each of the known tocotrienols, plus additional Tocol products. Theoretically, each novel tocotrienol and tocotrienol-like compound should be separable from the known tocotrienols and tocotrienols in the TRF using standard silica gel HPLC methodology. However, in the case of rice bran, a complex mixture results. This resultant mixture contained 3,4-dihydro-2-methyl-2-(4,8,12-trimethyltrideca-3'(E),7'(E),11'-trienyl)-2H-1-benzopyran-6-ol), a known tocotrienol that eluted by HPLC after about 21 minutes under the specified conditions. For that reason, we refer to this compound as "$P_{21}$". In addition, the mixture contained 3,4-dihydro-2-(4, 8,12-trimethyltrideca-3'(E), 7'(E),11'trienyl)-2H-1-benzopyran-6-ol), or "$P_{25}$", a novel tocotrienol that eluted by HPLC after about 25 minutes. And the mixture contained an apparent sterol which had a UV absorption maximum at 315 nm that eluted by HPLC after about 20 minutes ("$P_{20}$"). These three compounds cannot be separated using standard silica gel HPLC techniques.

Accordingly, the present invention includes novel techniques to purify tocotrienols and tocotrienol-like compounds from contaminants that cannot be removed using a silica column. These techniques are especially well suited for separating tocotrienols and tocotrienol-like compounds from sterol and other waxy contaminants. In one process, the TRF is dissolved in an appropriate solvent, preferably hexane, and then bound to an amine or cyano column (1 ml). We prefer to use a Bond Elute amine or cyano column. The tocotrienols and tocotrienol-like compounds of this invention may then be selectively eluted from the column by an appropriate solvent system. Preferably, this solvent system is a gradient of isopropanol in hexane. Using a small concentration of the polar solvent in the non-polar solvent (preferably about 0.5% isopropanol in hexane) known tocotrienols and tocotrienols may be eluted, while the novel tocotrienols and tocotrienol-like compounds of this invention are retained on the amine column. Then, by increasing the concentration of the more polar solvent (preferably to about 3% isopropanol in hexane), the tocotrienols and tocotrienol-like compounds of this invention may be selectively eluted, while any sterol and waxy contaminants remain bound to the amine column. Finally, these contaminants may be eluted using a high polarity solvent system, such as 6–10% isopropanol in hexane. Using this procedure, the desirable tocotrienols and tocotrienol-like compounds may be effectively separated.

An alternative technique also increases the recovered yield of tocotrienols and tocotrienol-like compounds from a biological source. In this alternative procedure, a biological source, stabilized or unstabilized, is first extracted with methanol. This step removes many of the unbound contaminants. Then, heat and, optionally, pressure, are applied to the biological source to release the tocotrienols and tocotrienol-like compounds. Examples of heat sources include, but are not limited to radiant heat sources (i.e., visible light or radioactive materials), convectional heat sources, microwaves, radio-frequency, friction or shearing. The preferred heat source is microwave heat. Alternatively, freeze/thaw methods or mechanical grinding might also be employed before, during or after heat and/or pressure treatment. Alternatively, the tocotrienols and tocotrienol-like compounds may be released by the use of caustic agents, for example, acids, such as hydrochloric or sulfuric acid. According to an alternate embodiment, sonication or detergent treatment may be employed prior to, concurrently with, or following the heat, pressure or caustic agent treatment. Experiments using the techniques described herein that employ various combinations of heat, pressure and reaction conditions will readily indicate the preferred conditions for a given biological source.

In purified form, one of the preferred compounds of the present invention, $P_{25}$, exhibits greater biological activity as a cholesterol-lowering agent than any of the known tocotrienols: including $P_{21}$ (known also as "tocotrienol"), $\alpha$-$T_3$, $\beta$-$T_3$, $\gamma$-$T_3$ or $\delta$-$T_3$. We believe that the double bonds on the isoprenoid side chain comprise the active portion of these compounds because their presence decreases the effect of London forces between the lipid side chain in biological membranes. We also believe that the number and the position of the alkyl substituents on the aromatic ring system and the isoprenoid side chain make a difference in the biological activity—the fewer the number of alkyl substituents, the greater the activity. We believe that reducing the steric hindrance caused by the methyl groups allows $P_{25}$ to penetrate more deeply into the membrane. Accordingly, the membrane may become more highly organized and thus, less permeable. Under this hypothesis, the compounds of this invention which substitute hydrogen for methyl at the 2-position of the chromanol ring demonstrate increased biological activity. However, alterations at that and other positions are also envisioned, as several different mechanisms which result in increased biological activity may be involved.

Because of their ability to lower total serum cholesterol and low density lipoprotein-cholesterol and increase the HDL-/LDL-cholesterol ratio, the novel tocotrienols and tocotrienol-like compounds of this invention may be used in the prevention and treatment of diseases associated with high levels of cholesterol.

Advantageously, the compounds of this invention do not substantially alter the serum levels of other blood components that contribute to the biodegradation of cholesterol. For example, the compounds of this invention do not substantially reduce the activity of cholesterol 7$\alpha$-hydroxylase—the enzyme that is responsible for degradation of cholesterol into bile acids.

Examples of diseases associated with high levels of cholesterol that may be treated by the compounds of this invention include, but are not limited to, atherosclerosis, thrombosis, coronary artery disease and other forms of cardiovascular disease. In addition, the ability of the compounds of this invention to lower serum glucose levels may increase the insulin production in Type 2 diabetics.

The compounds of this invention may also be used to alter the serum or plasma levels of several other blood constituents. For example, these compounds lower the plasma levels of thromboxane $A_2$ and platelet factor 4. In addition, they may serve passively as simple antioxidants or actively by decreasing the release of superoxides by neutrophils and other cytotoxins or cytokines, mast cells, macrophages, endothelial tissue and other immunoregulatory tissues. Antioxidation is accomplished in at least two ways. First, by reducing arachidonic acid metabolites, the neutrophils reduce the levels of superoxide production. Second, these compounds scavenge radicals which are already present. Accordingly, they exert a protective effect on the endothelium, lipoproteins, smooth muscle cells and platelets. In addition, these compounds may also serve as antioxidants to prolong the shelf lives of products prone to oxidation, such as food products. Advantageously, the tocotrienols and tocotrienol-like compounds of this invention may also prevent oxidative degradation of food products which results in the formation of carcinogenic compounds in such food products.

The thromboxanes (whose plasma levels are decreased using the compounds of this invention) also induce platelet aggregation and vasoconstriction. Therefore, the tocotrienols and tocotrienol-like compounds of this invention may be used to reduce blood clotting in a wide variety of applications. For example, these compounds may be used to treat or prevent diseases, such as thrombotic diseases, cardiovascular disease, hypertension, pulmonary diseases and renal diseases. Specifically, the compounds of this invention may be used to prevent or reverse blood clots and lesions which may cause diseases such as myocardial infarction, stroke, pulmonary embolism, deep vein thrombosis, peripheral arterial occlusion and other blood system thromboses.

Tocotrienols and tocotrienol-like compounds are also capable of acting as antiatherogenic agents by inhibiting or reversing the oxidation of LDL and by protecting vascular tissue in general from oxidative damages. The oxidized form of LDL ("OX-LDL") is a major component in the formation of atheroma. Such formation commonly results in a narrowing of the arteries by atherosis plaques. While not wishing to be bound by theory, we believe that by reducing serum LDL levels, tocotrienols and tocotrienol-like compounds enhance the rate of metabolic LDL turnover and therefore, decrease the exposure of LDL to oxidative agents.

Tocotrienols and tocotrienol-like compounds also decrease the concentration of lipoprotein (a) in the blood. It has been well established that elevated concentrations of Lp(a) are correlated with early onset and progression of atherosclerosis, premature myocardial ischemia and rheumatoid arthritis. In fact, Lp(a) concentration is a more accurate indicator of coronary heart disease than LDL concentration. Lowering Lp(a) concentrations in individuals having high Lp(a) levels (above about 20 mg/dl) drastically reduces the probability of atherosclerosis and coronary heart disease. Significantly, Lp(a) levels, unlike LDL concentration, are not affected by low-fat diets or commercial available hypocholesterolemic agents.

Tocotrienols and tocotrienol-like compounds also exhibit diuretic activity—they are antagonistic to vasopressin and angiotensin II. Accordingly, these compounds are useful in the treatment and management, for example, of hypertension.

According to another embodiment of this invention, tocotrienol or tocotrienol-like compounds may be administered pre-operatively to a patient in order to prevent septic shock. Advantageously, tocotrienols and tocotrienol-like compounds may be used in the treatment of extracorporeal blood. As used herein, the term "extracorporeal blood" includes blood removed in line from a patent subjected to extracorporeal treatment, and returned to the patient in processes such as dialysis, or blood filtration or bypass timing surgery. And the term includes blood products which are stored extracorporeally for eventual administration to a patient. Such products include whole blood, platelet concentrates and any other blood fraction in which inhibition of platelet aggregation is desired.

According to another embodiment of this invention, tocotrienols and tocotrienol-like compounds may be formulated in compositions and methods for coating the surface of invasive devices, to lower the risk of platelet aggregation—for example, the surfaces of devices such as, vascular grafts, stents, catheters and artificial valves. Such devices may be coated with the tocotrienols and tocotrienol-like compounds using conventional methodologies including physical adsorption and chemical cross-linking.

Furthermore, we have found that the tocotrienols and tocotrienol-like compounds of this invention, the known tocotrienols, and mixtures thereof also reduce the levels of tumor necrosis factor in response to lipopolysacchardie stimulation, lower arachidonic acid in the tissues and reduce oxygen metabolites in the blood of animals and humans. These results point to an overall reduction in prostaglandins and leukotrienes, both of which are synthesized from arachidonic acid, and a possible reduction in interleukin-1. Accordingly, the compounds of this invention may be employed for a variety of uses. For example, they may be used to prevent endothelial injury, such as ischemic and reperfused myocardium and ulcers. In addition, the inhibition of tumor necrosis factor biosynthesis would also be accompanied by a decrease in inflammation—i.e., through inhibiting the respiratory bursts of neutrophils or through free radical scavenging. Therefore, the compounds of this invention and the known tocotrienols are also useful as antiinflammatory agents for the prevention and treatment of a wide variety of diseases and conditions involving minor, acute and chronic inflammation. These include, but are not limited to, fever, rheumatoid diseases, pain, functio laesa. hypertension and edema.

In addition to their role in inflammatory response, prostaglandins have also been shown to inhibit glucose-induced insulin release, increase glucose concentration and stimulate glucagon secretion. Consequently, use of the compounds of this invention typically leads to an increased insulin to glucagon ratio. Therefore, the novel tocotrienols and tocotrienol-like compounds of this invention, the known tocotrienols, and mixtures thereof, may be used to improve glucose intolerance in diabetes mellitus. They may also be used to restore acute glucose-induced insulin response in non-insulin-dependent diabetes mellitus.

In addition to the above-stated uses, the tocotrienols and tocotrienol-like compounds of this invention, the known tocotrienols, and mixtures thereof, may also be used to enhance the immune response in animals and humans. These compounds typically reduce the amount of fatty acids in biological tissues. Since fatty acid levels effect the immune system, the compounds of this invention may serve as immunoregulators. They may, for example, be used to increase antibody titers to foreign proteins.

In addition, the reductions in fatty acid, cholesterol, triglyceride and glucose levels effected by the compounds of this invention are obtained without attendant substantial weight loss. The result is an increased feed to protein conversion ratio. Therefore, the novel tocotrienols and tocotrienol-like compounds of this invention, the known tocotrienols, and mixtures thereof, are useful in increasing feed conversion efficiency.

Hypercholesterolemic diseases and conditions that may be treated using the compositions and mixtures described herein include, but are not limited to, arteriosclerosis, atherosclerosis, xanthomatosis, hyperlipoproteinemias, and familial hypercholesterolemia.

Thrombotic diseases and conditions that may be treated using such compositions include, but are not limited to, pulmonary disease, in general (such as reduced specific conductance, reduced dynamic compliance and constriction (contraction of smooth muscle), excess pulmonary fluids (such as pulmonary lymph, foam, or bronchoalveolar lavage), adult respiratory distress syndrome, astatis and rhinitic disease (such as pulmonary and systemic hypertension, pulmonary edema, fluid accumulation (neutrophil infiltration) and pulmonary vascular permeability), pulmonary vasoconstriction (associated, for example, with endotoxemia, gram-negative organisms, anaphylaxis, hemorrhagic shock or allergy to ragweed), cardiac ischemia, microembolic and/or frank occlusion, reocclusion following transluminal angioplasty, myocardial infarction, cardiopulmonary bypass associated dysfunction, vasoconstriction (pulmonary and peripheral), organ dysfunction, platelet consumption and/or activation (and subsequent decreased function, aggregation and decreased numbers), mitral valve pathology associated with acute perioperative pulmonary hypertension, chronic obstructive arterial disease caused by arteriosclerosis, Maurice Raynaud's syndrome—vasoconstriction, renal artery stenosis, myocardial infarction, stroke, pulmonary embolism, deep vein thrombosis, peripheral arterial occlusion and other blood system thromboses.

Antioxidizing uses include, but are not limited to, the treatment and prevention of endothelial injury, such as ischemic and reperfused myocardium. Because of their antioxidizing activity, the tocotrienols and tocotrienol-like compounds of this invention may also be used in treating and preventing cancerous conditions (by, for example, preventing cancer-causing mutations in the genetic material of an animal or a human).

Antiatherogenic diseases and conditions that may be treated using such compositions include, but are not limited to, arteriosclerosis, atherosclerosis, mydocardial infarction, ischemia (i.e., myocardial ischmica, brain ischemia and renal ischemia) and strokes.

Inflammatory diseases and conditions that may be treated using such compositions include, but are not limited to, essential hypertension, hypertension of congestive heart failure, renal dysfunction caused by reduced myocardia output, endotoxemia, chronic liver disease or hypertension, pulmonary inflammation in asthma, bronchitic, pneumonia or acute lung injury, rheumatic diseases (such as rheumatoid arthritis and systemic lupus crythematosus), inflammatory bowel disease (such as ulcerative colitis), irritable bowel disease (such as villous adenoma), gastrointestinal disorders caused by excess acids, pepsin or bile salts, Zollinger-Ellison syndrome, skin diseases or trauma (such as burns or acid or caustic injury), gout, Bartter's syndrome, fever, rheumatoid diseases, pain, functio laesa, hypertension and edema.

Immunoregulatory diseases and diseases that may be treated using the compositions of this invention include, but are not limited to, chronic fatigue syndrome, graft rejections, autoimmune diseases, such as AIDS, and other viral disease that weaken the immune system.

The compounds and mixtures described herein are useful in pharmaceutical compositions, foodstuffs and dietary supplements. Advantageously, these products are hypocholesterolemic, antithrombotic, antioxidizing, antiatherogenic, antiinflammatory and immunoregulatory agents.

Pharmaceutical compositions may take the form of tablets, capsules, emulsions, suspensions and powders for oral administration, sterile solutions or emulsions for parenteral administration, sterile solutions for intravenous administration and gels, lotions and cremes for topical application. The pharmaceutical compositions may be administered to humans and animals in a safe and pharmaceutically effective amount to elicit any of the desired results indicated for the compounds and mixtures described herein.

This invention also relates to prodrug forms of tocotrienol and tocotrienol-like compounds which, upon administration to a patient, undergo biotransformation into active form.

The pharmaceutical compositions of this invention typically comprise a pharmaceutically effective amount of a tocotrienol or tocotrienol-like compound of this invention, or a mixture thereof, and a pharmaceutically acceptable carrier. Such carriers may be solid or liquid, such as, for example, cornstarch, lactose, sucrose, olive oil or sesame oil. If a solid carrier is used, the dosage forms may be tablets, capsules or lozenges. Liquid dosage forms include soft gelatin capsules, syrup or liquid suspension.

Therapeutic and prophylactic methods of this invention comprise the step of treating patients in a pharmaceutically acceptable manner with the compositions and mixtures described herein. As used in this application, the term "pharmaceutically effective amount" or "cholesterol-lowering amount" refers to an amount effective to lower blood levels of LDL-cholesterol and total serum cholesterol, while increasing the ratio of HDL-cholesterol to LDL-cholesterol in the blood. Alternatively, the term "pharmaceutically effective amount" refers to an amount effective to decrease blood levels of LDL-cholesterol and total serum cholesterol associated with hypercholesterolemia, an amount effective for lipogenesis, an amount effective to inhibit platelet aggregation, an amount effective to decrease the release of superoxides by human peripheral blood neutrophils, an amount effective to reduce the level of tumor necrosis factor or interleukin-1, an amount effective to reduce the level of arachadonic acid, an amount effective to increase antibody titers in the blood, an amount effective for antithrombotic uses, an amount effective to treat, prevent or delay the onset of any one of the following diseases or conditions including inflammatory diseases, immunoregulatory disease, fever, edema, diabetes mellitus, cancer, signs of aging, pain, septic shock, chronic fatigue syndrome and functio laesa; or an amount effective to decrease the concentration of Lp(a) in the blood or to increase food conversion efficiency.

The pharmaceutical compositions of this invention may be employed in a conventional manner for the treatment and prevention of any of the aforementioned diseases and conditions. Such methods of treatment and prophylaxis and their dosage levels and requirements are well-recognized in the art and may be chosen by those of ordinary skill in the art from the available methods and techniques. Dosage ranges may be from about 1 to about 1000 mg/day. However, lower or higher dosages may be employed. Specific dosage and treatment regimens will depend upon factors such as the patient's health status, the severity and course of the patient's disease or disposition thereto and the judgement of the treating physician.

Tocotrienols and tocotrienol-like compounds and mixtures thereof may also be used in combination with conventional therapeutics used in the treatment or prophylaxis of any of the aforementioned diseases. Such combination therapies advantageously utilize lower dosages of those conventional therapeutics, thus avoiding possible toxicity incurred when those agents are used as monotherapies. For example, tocotrienols or tocotrienol-like compounds may be used in combination with bile acid sequestrants, such as Cholestyramine and Colestipol; fibric acid derivatives, such as, Clofibrate, Gamfibrozil, Bezafibrate, Fenofibrate, and Ciprofibrate; HMGR inhibitors, such as Lovastatin, Mevastatin, Pravastatin, Simvastatin and SRI-62320; Probucol, Nicotinic Acid; its derivatives and conjugates, such as, 6-OH-Nicotinic Acid, Nicotinaria Acid, Nicotinamide, Nicotinamide-N-oxide, 6-OH-Nictinamide, NAD, N-Methyl-2-pyridine-8-carboxamide, N-Methyl-Nicotinamide, N-Ribosy-2-Pyridone-S-Carboxide, N-Methyl-4-pyridone-5-carboxamide, Bradilian, Niceritrol, Sorbinicate and Hexanicit; Neomycin and d-Thyroxine.

In foodstuffs, tocotrienols, and tocotrienol-like compounds, and mixtures thereof, may be used with any biologically acceptable carrier to provide safe and effective means of lowering blood levels of LDL-cholesterol and total serum cholesterol, while increasing the ratio of HDL-cholesterol to LDL-cholesterol in the blood. In addition, the foodstuffs may be used to inhibit platelet aggregation, to decrease the release of superoxides by human peripheral blood neutrophils, to reduce the levels of tumor necrosis factor and interleukin-1, to increase antibody titers in the blood, or to treat, prevent or delay the onset of one or more of the following disease or conditions: immunoregulatory disease, inflammation, fever, edema, diabetes mellitus, cancer, signs of aging, pain, rheumatoid disease, septic shock, chronic fatigue syndrome and functio laesa. Alternatively, they may be used to decrease Lp(a) concentrations in the blood or to increase feed conversion efficiency.

Foodstuffs containing the tocotrienols and tocotrienol-like compounds according to this invention, and mixtures thereof, may be combined with any other foodstuff. For example, oils containing the compounds of this invention may be used as cooking oil, frying oil, or salad oil and may be used in any oil-based food, such as margarine, mayonnaise or peanut butter. Grain flour fortified with the compounds of this invention may be used in foodstuffs, such as baked goods, cereals, pastas and soups. Oils containing tocotrienols and tocotrienol-like compounds can be emulsified and used in a variety of water-based foodstuffs, such as drinks, including drink mixes. Advantageously, such foodstuffs may be included in low fat, low cholesterol or otherwise restricted dietary regimens.

The pharmaceutical compositions and foodstuffs of this invention may be administered to humans and animals such as, for example, liverstock and poultry. Once an animal has ingested or otherwise been administered a tocotrienol or tocotrienol-like compound, or a mixture thereof, it advantageously retains the hypercholesterolemic, antithrombotic, antioxidizing, antiinflammatory, antiatherogenic, immunoregulatory and other advantageous biological activities of the administered compounds. Therefore, such an animal, or any product derived therefrom, such as, for example, milk, may be consumed by a human or another animal to derive the benefits of the tocotrienols and tocotrienol-like compounds. For example, a chicken which ingests a grain or meal fortified with the compounds of this invention may later be eaten by a human to derive the cholesterol-reducing benefits.

In addition, the administration of tocotrienols or tocotrienol-like compounds to animals results in an increase in feed conversion efficiency. In higher fat content animals, such as cattle, swine, sheep and lamb, tocotrienols or tocotrienol-like compounds advantageously lead to faster growth, lower cholesterol content, and higher percentage lean meat. When administered to fowl, tocotrienols and tocotrienol-like compounds result in production of eggs characterized by reduced cholesterol content of the yolk and higher protein content of the egg white.

In order that this invention be more fully understood, the following examples are set forth. These examples are for purposes of illustration only, and are not to be construed as limiting the scope of the invention in any way.

In these examples, mass spectra data was acquired using Model MS-902 manufactured by and obtainable from Associate Electrical Industries, Ltd. (Department of Chemistry, University of Wisconsin, Madison). Samples were introduced directly into the ion source on a glass probe at 100° C. The potential of the ionizing electrical beam was 70 e.v. NMR in $CDCl_3$ were obtained using NMR-500 by Biukr, FDR at room temperature. IR was done as thin film using a Perkin Elmer instrument. Centrifugation was done in an Eppendorf Centrifuge (model 1240). Microwaving was done in a Whirlpool household oven (Model No. MT6901XW-O operating at 800 watts. HPLC was done using a Waters pump 6000A or a Gilson pump 307, a Shimadzu fluorescence detector RF-535 and integrator CR3A, a Gilson's autoinjector, Perkin Elmer 50A UV detector or a Shimadzu SPD-10 AV UV-VIS spectrum photometric detector and a Kipp and Zonen BD41 recorder. Unless otherwise indicated, the following HPLC conditions were employed: 20 µl injections, Porasil column (Waters column, 10µ, 4 mm×30 cm) using an isocratic system of hexane and isopropanol (99.75%:0.25%, v/v) at a flow rate of 1.3 ml/min. Detection was done at an exitation wavelength of 295 nm and an emission wavelength of 330 nm (fluorescence detector) and UV absorption at 295 nm.

All assays conducted on chicken or swine serum were done following the protocols described in A. A. Qureshi et al., "Lowering Of Serum Cholesterol In Hypercholesterolemic Humans By Tocotrienols" (Palmvitee), *Am. J. Clin. Nutr.*, 53, pp. 1021S–26S (1991). All enzymatic assays were done following the protocols described in A. A. Qureshi et al., "Effects of Cereals and Culture Filtrate of Trichoderma viride on Lipid Metabolism of Swine", *Lipids*, 17, pp. 924 (1982). Plasma insulin, glucagon and TNF levels were measured using radioinnumoassay kits from Ventrex Laboratories, Inc. (Portland, Me.), ICN Biomedicals, Inc. (Costa Mesa, Calif.) and Genzyme Corp. (Cambridge, Mass.), respectively.

EXAMPLE 1

The following protocol may be employed for carrying out the stabilization of a biological source, using rice bran as the sample.

Rough rice (paddy rice) from a farm is dried in a commercial-type continuous flow, non-mixing, heated air dryer. Drying is carried out to lower the moisture content of the rice from a level of between about 18 and 22 percent to a level between about 10 and 13 percent. The dried rice is then cleaned by removing dust, stones, seeds and sticks by aspiration in a commercial rice cleaning machine, followed by gravity separation in a stoner and particle size separation in a disk grader and a drum separator. The husks are then removed using a rubber roller sheller. Paddy (husks or hulls) are removed using a paddy separator. The raw bran is then removed in a friction mill to yield polished rice. The raw bran is then pneumatically conveyed either to the extruder or to storage until stabilization.

To carry out stabilization, the raw bran is pneumatically conveyed to a filter/sifter to remove residual broken rice. After sifting, the raw bran is pneumatically conveyed to a mixing/tempering hopper tank. The raw bran is conveyed from the discharge of the mixing tank to the extruder inlet valve of a clamped barrel single screw extruder by a metered screw conveyer feeder. The operating conditions of the extruder are maintained during stabilization in the following range:

flow rate: 900–2000 lbs/hr
pressure: 800–2000 PSI
temperature: 135°–210° C.
time: 5–90 seconds.

The dry heat stabilized raw bran is then fed directly into the feed hopper of an expander cooker. Alternatively, the feed to the cooker may be raw bran that has been cooled with dry ice. Within the extruder, the bran is conveyed by a discontinuous worm shaft toward the discharge plate at a rate of around 341 lbs/hr. Water and steam are added through injection ports in the barrel of the extruder at a rate of around 38 lbs/hr to completely mix the material and to raise the moisture level. The ambient temperature is about 30° C. Flow of the material is controlled by a discharge die plate at a rate of about 341 lbs/hr. The feed material moisture level is maintained at about 11.4% and the temperature is held between about 90° and 135° C. for between about 15 and 90 seconds. The moisture level in the collet produced is about 14% at a discharge temperature of 125° C.

As the bran is extruded through the die plate, the sudden decrease in pressure causes the liquid water to vaporize. During cooking, enzymes are denatured and some constituents of the bran are gelatinized into a fluid paste which binds the particles together. A compact pellet is formed. Vaporization of water causes breakage within the cells ideally suited for solvent migration percolation. The introduction of steam and water during the process raises the moisture content of the bran to about 22–25 percent. The extruder discharge is then sent downstream at a rate of around 341 lbs/hr. to a dryer/cooler. Moisture flow to the extruder is maintained at about 96 lbs/hr and the temperature is kept in the range of 82° C. to 130° C. The discharge from the dryer/cooler is maintained at a rate of about 341 lbs/hr and at a moisture level of about 8%. Stabilized rice bran is the result. These conditions also allow for storage of the stabilized bran.

The stabilized bran is immersed in hexane in a ratio by weight of about two to one. Typically, about 10–100 g of material can be extracted using this protocol. The hexane is generally heated to about 60° C. using a steam table incorporated into an explosion proof vented hood, but other solvents and other temperatures may also be employed. The hexane/oil miscella is removed from the bran by filtration. About 5–6 washings are necessary to bring the oil content of the bran to less than one percent. The defatted bran and the hexane/oil miscella are both desolventized under gentle heating with steam.

If 100–500 lbs. of stabilized bran is to be extracted, it is more practical to use the following protocol. The stabilized bran is fed into a counter-current extractor at a flow rate of about 111 lbs/hour. Fresh hexane is introduced at a rate of around 312 lbs/hr. The fresh solvent (hexane) temperature is maintained at about 50° C., while the extractor temperature is maintained at around 52° C. Residence time in the extractor is typically around 45 minutes. The product is a defatted bran with an oil content of less than one percent. The hexane/oil miscella exiting the discharge of the extractor is filtered through a plate and frame filter press. The filtered miscella is then pumped to a steam heated still where the hexane is evaporated and collected by a condenser for reuse.

Following extraction and desolventization, the crude rice bran oil is typically degummed, dewaxed, bleached and physically refined using steam distillation. Degumming is carried out by a two stage addition under agitation of 2% water by weight and then 0.15% phosphoric acid (85% reagent grade) by weight. The temperature is held at about 82° C. to 88° C. for 10 minutes and the sludge containing the gums is then removed via ultrafugation. (See, e.g., U.S. Pat. No. 4,049,686). The degummed bran is cooled to about 5° C. to 8° C. and held for 24 hours. The dewaxed oils form a layer above the waxes which can be decanted using a vacuum pump. Bleaching is carried out according to the official American Oil Chemist's Society method 6c 8a–52. Physical refining is carried out in a glass deodorizer at about 250° C. and around 3 mm Hg for about 2 hours.

The following specific protocols are referred to in the subsequent examples. Stabilization protocols follow the general method set forth above, with the precise conditions defined as follows:

Protocol I-Dry Heat Stabilization

| Extruder: Wenger Model X-25 Standard Screw/Barrel Setup: | | | |
|---|---|---|---|
| Barrel # | Standard Port | Screw # | Standard Port |
| 5 | 28714-9 | 5 | 28320-1 |
| 4 | 28318-1 | 4 | 8326-9 |
| 3 | 28372-9 | 3 | 28326-1 |
| 2 | 28318-1 | 2 | 28326-5 |
| 1 | 28350-1 | 1 | 28387-9 |

| Standard Die Setup: | | |
|---|---|---|
| Die/Spacer | Measurement | Standard Port |
| Spacer | 0.375 | 28340-11 |
| Back Plate | 0.625 | 28361-51 |
| Intermediate Plate | 0.218 | 28316-723 |
| Front Plate | 0.235 | 28389-507 |

| Operating Conditions: | |
|---|---|
| Feed Rate: | 1000 lbs/hr |
| Temperature: | 170° C. at exit die |
| Pressure: | 975–1025 psi |
| Moisture Feed: | 12% |
| Moisture Discharge: | 9.6% |
| Residence Time: | 15 seconds |
| Run Duration: | 8 hours |
| Sample Size: | 50 lbs. |

Protocol II-Dry Heat Followed by Wet Heat Stabilization

| | |
|---|---|
| Dry Heat Stage: | Protocol I |
| Wet Heat Stage: | |
| Extruder: | Anderson 4 inch |
| Screw/Barrel Configuration: | Standard Cut Flight |
| Die Setup: | |
| Diameter: | 0.1875 inches |
| Land: | 0.75 inches |
| Operating Conditions: | |
| Feed Rate: | 378 lbs/hr |
| Shaft Speed: | 279 rpm |
| Steam injection: | 36 lbs/hr (32 psi at #8 hole) |
| Mechanical Pressure: | 750 psi (est.) |
| Moisture Feed: | 11.4% |
| Discharge Moisture: | 15% |
| Discharge Rate: | 450 lbs/hr |
| Discharge Temp.: | 121° C. |

Protocol III-Drying/Cooling Procedure

The wet heat stabilized product of protocol II (15% moisture) was discharged onto aluminum trays and placed in a tray oven at 101.1° C. until the moisture content was 8–10% (approximately 1.5 hours). The trays were then placed on tray racks and allowed to cool at ambient temperature (approximately 20° C.).

Protocol IV-Oil Extraction (Laboratory Method)

| | |
|---|---|
| Oil to hexane ratio: | 1:4 |
| # of washings: | 3 |
| Extraction temperature: | 40° C. |

The hexane was removed from the extract by mild heating (40° C.) under a mild vacuum.

Protocol V-Oil Extraction (Pilot Plant Method)

| | |
|---|---|
| Oil to hexane ratio: | 1:4 |
| # of washings: | 6 |
| Extraction temperature: | 60° C. |
| Amount Extracted: | 20 lbs |
| Yield: | 16 lbs defatted bran |
| | 4 lbs crude oil |

The hexane was removed from the extract by heating to 115.5° C.

Protocol VI-Oil Extraction (Cold Extraction)

| | |
|---|---|
| Oil to hexane ratio: | 1:4 |
| # of washings: | 6 |
| Extraction temperature: | 20° C. (ambient) |
| Amount Extracted: | 20 lbs |
| Yield: | 16.4 lbs defatted bran |
| | 3.6 lbs crude oil |

The hexane was removed from the extract by heating to 115.5° C.

Protocol VII-Dewaxing 20 lbs of crude oil were refrigerated for 24 hours at 4° F. (−15.6° C.). The supernatant, which contained the dewaxed oil, was decanted from the solidified waxes. The waxes were then centrifuged to remove entrained oil yielding waxes (0.59 lbs) and dewaxed oil (19.407 lbs).

EXAMPLE 2—Purification of $P_{25}$

The rice bran was stabilized according to protocol I. 1.0 g of the stabilized rice bran was ground into a fine powder and extracted with 8 ml of methanol in a disposable screw capped tube using a shaker for ~30 minutes. The suspension was then centrifuged at 2000 rpm for 10 min. to recover the methanol layer, which was evaporated under vacuum at 40° C. The remaining dried residue was then extracted with 4 ml hexane by shaking on a shaker for 3 min. followed by centrifugation at 2000 rpm for 5 min. The resulting supernatant was transferred into an injection vial, which was capped and centrifuged again for 2 min. Evaporation yielded the TRF.

Ten mg of the TRF, which contained novel tocotrienol $P_{25}$, was dissolved in 0.5 ml of hexane and bound to a Bond Elute Amine column (1.0 ml) that was first equilibrated with 2 ml hexane. The column was then washed with 1 ml of hexane, followed by 1 ml of 3% isopropanol in hexane. This step removed most of the known Tocol products. Then 1.0 ml of 5% isopropanol in hexane was run through the column. The recovered solution was evaporated, yielding 1.85 mg of $P_{25}$ and 0.44 g of tocotrienol ($P_{21}$). Finally, 1.0 ml of 6% isopropanol in hexane followed by 1.0 ml 10% isopropanol in hexane was run through the column. The resultant fractions were analyzed by HPLC. No trace of the $P_{20}$ impurity was visible on the HPLC trace.

EXAMPLE 3

Amine column purified compounds from Example 2 were further purified by HPLC to separate tocotrienol ($P_{21}$) and $P_{25}$. The peak fractions from several runs were collected and analyzed by HPLC. The purified samples each showed a single symmetrical peak as observed by UV and fluorescence. The following analytical data was obtained for tocotrienol ($P_{21}$) and $P_{25}$:

Tocotrienol $P_{21}$:

MS(EI): m/e $382^+$(molecular ion)
$163^+$
$123^+$

NMR (CDCl$_3$):

δ 1.26(s, H), 1.50–1.84(m, 4H), 1.58
(s, 9H), 1.66(s, 3H), 1.90–2.15(m, 10H), 2.69(t, J=
6.7 Hz, 2H), 4.23(s, 1H), 5.07(m, 3H), 6.51–6.57(m,
2H), 6.63(d, J=8.5 Hz, 1H).

IR (film):

(cm$^{-1}$) 3400, 2990, 2950, 2876, 1500,
1458, 1240, 750.

The MS data correspond to a molecular formula of $C_{26}H_{38}O_2$. The pattern is characteristic of the fragmentation observed with α-, β-, and γ-tocotrienols as reported by Rao et al., "Identification and Estimation of Tocopherols and Tocotrienols in Vegetable Oils Using Gas Chromatography-Mass Spectrometry", *J. Agr. Food Chem.*, 20(2), pp.240–245 (1972). The peak at m/e $163^+$ indicates loss of the side chain $(C_{16}H_{27})^+$ giving rise to the ion $C_{10}H_{11}O_2$ (163.0759). The peak m/e $123^+$ originates from the cleavage of the side chain by the breakdown of the chroman structure with hydrogen rearrangement and loss of a methyl acetylene fragment ($CH_3—C≡CH_2$).

The NMR spectra is identical to that of $T_3$, except that the methyl group on the benzene ring at δ 2.2 normally present in $T_3$ is missing in the spectrum of $P_{21}$.

The IR indicates the presence of a phenolic OH group at 3700 cm$^{-1}$, a benzene ring at 1650 cm$^{-1}$ and a chroman ring at 1680 cm$^{-1}$.

Based on these data, the structure of $P_{21}$ was identified as desmethyl-tocotrienol (3,4-dihydro-2-methyl-2-(4,8,12-trimethyltrideca-3' (E),7'(E),11'-trienyl)-2H-1-benzopyran-6-ol):

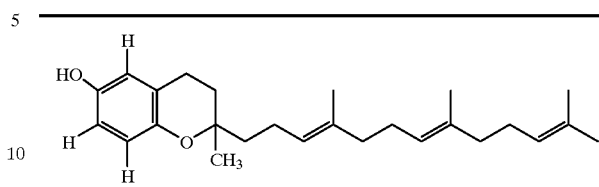

$P_{25}$:

MS (EI): m/e $386^+$ (molecular ion)
$175^+$
$149^+$
$123^+$

NMR (CDCL$_3$): δ 1.58(s, 3H), 1.59(s, 3H), 1.62(s, 3H), 1.67(s, 3H), 1.73(m, 2H), 1.90–2.08(m, 10H), 2.19(m, 2H), 2.63–2.85(m, 2H), 3.89(m, 1H), 4.30(br. s, 1H), 5.07(m, 2H), 5.14(t, J=7.9Hz, 1H), 6.51(d, J=2.9Hz, 1H), 6.56(d of d, J=2.9, 8.6Hz, 1H), 6.66 E(d, J=8.6Hz, 1H).
IR (film): (cm$^{-1}$) 3388, 2924, 1494, 1450, 1352, 1280, 1218, 1080.

The MS data correspond to a molecular formula of $C_{25}H_{36}O_2$. The pattern is characteristic of the fragmentation observed for γ-tocotrienol, except that the methyl on the chroman ring adjacent to oxygen is missing.

The NMR spectra is similar to that of desmethyl-$T_3$.

The IR indicates the presence of a phenolic OH group at 3388 cm$^{-1}$, a benzene ring at 1494 cm$^{-1}$ and a chroman ring at 1352 cm$^{-1}$.

Based on that data, the structure of $P_{25}$ was identified as didesmethyl-tocotrienol (3,4-dihydro-2-(4,8,12-trimethyltrideca-3'(E),7'(E),11'-trienyl)-2H-1-benzopyran-6-ol):

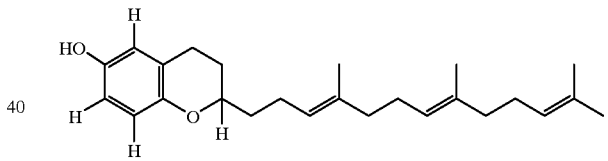

EXAMPLE 4

Isolation and Purification of $P_{16}$ and $P_{18}$

The rice bran was stabilized according to protocol I. 1.0 g of the stabilized rice bran was ground into a fine power and microwaved for 3 minutes (in 1 minute intervals) to release any bound $T_3$ and $T_3$like compounds. The microwaved rice bran was then extracted with 7 ml of methanol in a disposable screw capped tube using a shaker for ⁻300 minutes. The suspension was then centrifuged at 2000 rpm for about 5 minutes. The supernatant was removed and the methanol was evaporated under vacuum at 40° C. The resulting residue contained a mixture of free and previously bound $T_3$ and $T_3$-like compounds.

The residue was dissolved in 250 μl (200 mg) of hexane and applied to a 1 ml Bond Elute amine column that was first equilibrated with 2 ml of hexane. The column was then washed with 1 ml of hexane. Then 0.5 ml aliquots of the following solvents were eluted through the column successively: 0.5% isopropanol in hexane, 1.0% isopropanol in hexane, 1.5% isopropanol in hexane, 2.0% isopropanol in hexane, 2.5% isopropanol in hexane and 3% isopropanol in hexane. Finally, the column was washed with 0.5 ml of 10% isopropanol in hexane. The resultant fractions were analyzed and the fractions containing $P_{16}$ and $P_{18}$ were combined (only the fractions collected using 1.5%–3% isopropanol in hexane contained $P_{16}$ and $P_{18}$ in significant amounts).

In order to separate $P_{16}$ and $P_{18}$, HPLC conditions identical to those described in this application were used, except that the concentration of isopropanol was increased from 0.25% to 0.5% in hexane. Under those conditions, $P_{16}$ eluted at 13 minutes and $P_{18}$ eluted at 15 minutes. The peak fractions were collected and analyzed by HPLC. These purified samples each showed a single symmetrical peak as observed by UV and fluorescence. The following analytical data was obtained for $P_{16}$ and $P_{18}$:

$P_{16}$:

| | | |
|---|---|---|
| MS(EI): | m/e | $380^+$ (molecular ion) |
| | | $161^+$ |
| molecular formula: | $C_{27}H_{40}O$ | |
| molecular weight | (actual): | 380.3084 |
| | (calculated): | 380.3079 |

The fragmentation pattern was similar to that of $P_{21}$ and $P_{25}$. The peak at m/e 161+ indicates loss of the $C_{16}H_{27}$ side chain giving rise to $C_{11}H_{13}O$. Based on these data, the following structure for $P_{16}$ was identified:

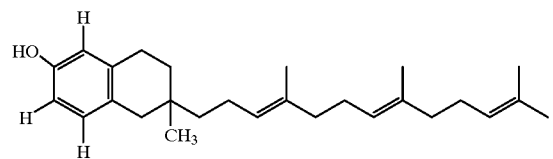

$P_{18}$:

| | | |
|---|---|---|
| MS (EI): | m/e | 424+ (molecular ion) |
| | | 205+ |
| molecular formula: | $C_{28}H_{40}O_3$ | |
| molecular weight (actual): | | 424.3010 |
| (calculated): | | 424.2977 |

The fragmentation pattern was again similar to that of $P_{21}$ and $P_{25}$. Based upon these data, the following structure for $P_{18}$ was identified:

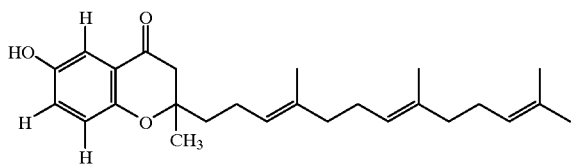

EXAMPLE 5

The effects of different rice brans on the serum levels of total cholesterol, HDL-cholesterol, LDL-cholesterol, apolipoprotein $(a)_1$ and apolipoprotein B was determined in chickens.

The following protocols were performed to yield the samples displayed in Table I:

entry 5: protocol I entry 6: protocol I, followed by protocol IV.

All other samples were obtained from commercially available sources.

Chickens were chosen as our initial model because they synthesize cholesterol in the liver using a mechanism similar to that of humans (unlike rats and mice that synthesize cholesterol in the intestines). Each group of chickens (6-week old female white leghorn) was administered either a chick mash control diet or a control diet containing a 20% equivalent of a test rice bran. The amount of feed consumed by all groups was comparable to the control group and the feeding period was 4 weeks. The birds were fasted for a period of 14 hours prior to sacrifice (at 0800 hours).

The chicken mash diet contained the following ingredients:

| Ingredients | Weight (g) |
|---|---|
| Corn (8.8% protein) | 615.0 |
| Soybean Meal | 335.0 |
| Corn Oil | 10.0 |
| Calcium Carbonate | 10.0 |
| Dicalcium Phosphate | 20.0 |
| Iodized Salt | 5.0 |
| Mineral Mixture[a] | 2.5 |
| Vitamin Mixture[b] | 2.5 |

[a]Mineral mixture contained per kg feed: zinc sulfate · $H_2O$, 110 mg; manganese sulfate $5H_2O$, 70 mg; ferric citrate · $H_2O$, 500.0 mg; copper sulfate · $5H_2O$, 16.0 mg; sodium selenite, 0.2 mg; DL-methionine, 2.5 g; choline chloride (50%), 1.5 g; ethoxyquin (1,2-dihydro-6-ethoxy-2,2,4-trimethylquinoline), 125 mg; and thiamine-HCl, 1.8 mg.
[b]Vitamin mixture contained per kg feed: vitamin A, 1,500 units; vitamin $D_3$, 400 units; vitamin E, 10 units, riboflavin, 3.6 mg; calcium pantothenate, 10.0 mg; niacin, 25.0 mg; pyridoxine-HCl, 3.0 mg; folacin, 0.55 mg; biotin, 0.15 mg; vitamin $B_{12}$, 0.01 mg; and vitamin $K_1$, 0.55 mg.

The results are displayed below in Table I. Percentages of increases or decreases are shown in parentheses.

TABLE I

| | Concentration in Serum (mg/100/ml) | | | | |
|---|---|---|---|---|---|
| Nutritional State[1] | Total Chol. | HDL-Chol. | LDL-Chol. | Apo-$A_1$ | Apo-B |
| 1) Control Group Chick Nash (CTL) | 165.9 ± 6.9[A] (100.0) | 104.2 ± 4.65[A] (100.0)[2] | 47.9 ± 4.64[A] (100.0) | 132.9 ± 3.88[A] (100.0) | 31.4 ± 1.68[A] (100.0) |

TABLE I-continued

Concentration in Serum (mg/100/ml)

| Nutritional State[1] | Total Chol. | HDL-Chol. | LDL-Chol. | Apo-A$_1$ | Apo-B |
|---|---|---|---|---|---|
| 2) Cellulose (20% Equ.) | 155.4 ± 3.5[B] (93.7) | 96.0 ± 4.99[A] (92.1) | 42.6 ± 4.12[B] (88.9) | 126.8 ± 3.81[A] (95.4) | 30.4 ± 1.31[A] (96.8) |
| 3) California Rice Bran (20% Equ.) | 151.2 ± 3.7[B] (91.1) | 100.4 ± 5.42[A] (96.4) | 39.0 ± 4.22[A,B] (81.4) | 125.8 ± 4.78[A] (94.7) | 28.8 ± 1.54[A] (91.7) |
| 4) Louisiana Rice Bran (20% Equ.) | 142.0 ± 4.3[C] (85.6) | 101.7 ± 6.41[A] (97.6) | 34.6 ± 3.09[B] (72.2) | 132.0 ± 3.84[A] (99.3) | 27.6 ± 1.41[B] (87.9) |
| 5) Louisiana Rice Bran Stabilized (20% Equ.) | 128.5 ± 4.0[D] (77.5) | 98.1 ± 7.25[A] (94.1) | 31.4 ± 2.72[B] (65.6) | 133.3 ± 3.32[A] (100.2) | 25.7 ± 2.25[B] (81.8) |
| 6) Louisiana Rice Bran Defatted (20% Equ.) | 148.5 ± 6.1[D] (89.5) | 100.2 ± 4.69[A] (96.2) | 42.4 ± 3.01[A] (88.5) | 125.7 ± 5.56[A] (94.6) | 28.7 ± 1.31[A] (91.4) |
| 7) Commercial Rice Bran (20% Equ.) | 150.0 ± 4.6[B] (90.4) | 98.9 ± 6.89[A] (94.9) | 40.6 ± 3.88[A] (84.8) | 125.1 ± 5.56[A] (94.1) | 29.0 ± 1.26[A] (92.4) |

[1]Feeding period was 4 weeks; time of killing was 0800 hours. The birds were fasted for 14 hours prior to killing. Data expressed as means ± SD; n = 6 chickens per group.
[2]Percentages of increases or decreases are in parentheses.
[A-D]Values not sharing a common superscript letter are different at $P < 0.01$.

The diet which included stabilized rice bran demonstrated superior cholesterol reducing activity when compared with the other diets. It advantageously lowered the LDL-cholesterol level by almost 35%, while lowering the HDL-cholesterol level by only 5.9%, as compared to the control diet. In addition, it increased the ratio of apolipoprotein $(a)_1$ to apolipoprotein B by 21%. This ratio is used as an indicator for assessment of risk for coronary heart disease (see Naito et al., "The Clinical Significance Of Apolipoprotein Measurements," *J. Clin. Immunoassay,* 9(1), pp. 11–20 (1986)).

EXAMPLE 6

We next determined the effects of different rice brans on the hepatic enzymatic activities of HMG-CoA reductase, cholesterol 7α-hydroxylase and fatty acid synthetase, and the serum levels of triglycerides and glucose in chickens fed with them. The feeding conditions were identical to those described in Example 5. The samples were prepared as described in Example 5.

The results are displayed below in Table II. Percentages of increases and decreases are shown in parentheses.

TABLE II

Hepatic Enzymatic Activities

| Nutritional State[1] | HMG-CoA Reductase (pmoles/mg/min)[3] | Cholesterol 7α-Hydroxylase (nmoles/mg/min)[4] | Fatty Acid Synthetase (nmoles/mg/min)[5] | Serum Triglycerides (mg/100 ml) | Serum Glucose (mg/100 ml) |
|---|---|---|---|---|---|
| 1) Control Group Chick Mash (CTL) | 405.3 ± 15.5[A] (100.0)[2] | 0.808 ± 0.062[A] (100.0)[2] | 69.0 ± 3.40[A] (100.0) | 75.7 ± 3.34[A] (100.0) | 109.8 ± 3.50[A] (100.0) |
| 2) Cellulose (20% Equ.) | 417.0 ± 14.6[A] (102.9) | 0.882 ± 0.031[A] (109.2) | 58.7 ± 2.25[B] (85.1) | 69.4 ± 2.93[B] (91.7) | 100.9 ± 1.89[B] (91.8) |
| 3) California Rice Bran (20% Equ.) | 340.2 ± 17.6[B] (83.9) | 0.851 ± 0.093[A] (105.3) | 55.1 ± 4.59[B] (79.9) | 65.4 ± 2.84[B,C] (86.4) | 96.1 ± 0.94[A,B] (87.5) |
| 4) Louisiana Rice Bran (20% Equ.) | 330.5 ± 12.8[B] (81.5) | 0.935 ± 0.044[B] (115.7) | 68.7 ± 3.88[A] (99.6) | 63.2 ± 1.61[C] (83.5) | 93.1 ± 2.20[C] (84.8) |
| 5) Louisiana Rice Bran Stabilized (20% Equ.) | 311.7 ± 14.6[B] (76.9) | 0.939 ± 0.039[B] (116.2) | 65.6 ± 5.69[A] (95.1) | 63.9 ± .92[C] (84.5) | 90.4 ± 1.38[C] (82.3) |
| 6) Louisiana Rice Bran Defatted (20% Equ.) | 388.7 ± 14.8[C] (95.9) | 0.852 ± 0.028[A] (105.4) | 70.4 ± 2.12[A] (102.0) | 72.3 ± 1.67[A] (95.6) | 99.3 ± 1.63[A] (90.4) |
| 7) Commercial Rice Bran (20% Equ.) | 371.2 ± 15.5[C] (91.6) | 0.850 ± 0.036[A] (105.2) | 64.7 ± 3.66[A] (93.8) | 70.9 ± 1.61[A] (93.7) | 101.2 ± 1.21[A] (92.1) |

[1]Feeding period was four weeks; time of killing was 0800 hours. The birds were fasted for 14 hours prior to killing. Data expressed as means ± SD; n = 6 chickens per group.
[2]Percentages of increases or decreases are in parentheses.
[3]p-moles of mevalonic acid synthesized per minute per mg of microsomal protein.
[4]n-moles of [$^{14}$c]-cholesterol into [$^{14}$c] 7-α-hydroxycholesterol per minute per mg of microsomal protein.
[5]n-moles of NADPH oxidized per minute per mg of cytosolic protein.
[A-C]Values not sharing a common superscript letter are different at $P < 0.01$.

As shown in Table II, the diet which contained stabilized rice bran produced a marked reduction (over 23% as compared to the control diet) in the activity of HMG-CoA reductase, the rate-limiting enzyme of cholesterol biosynthesis. However, the activity of enzyme responsible for the degradation of cholesterol, cholesterol 7α-hydroxylase, was not substantially affected. Furthermore, this diet reduced the serum levels of triglycerides (fats) and glucose by 15.5% and 17.7%, respectively.

EXAMPLE 7

We next compared the effects of rice bran oils extracted from various sources on serum lipid parameter of chickens fed with diets supplemented with those oils. Each group of 6 chickens (6-week old female white leghorn) was fed the chicken mash diet described in Example 5 for 14 days. Following this period, the chickens were fed a diet consisting of the chicken mash diet containing a 5% supplement of various oils. The control diet included a supplement of 5% corn oil. After 4 weeks, the birds were fasted for 36 hours and then refed for 48 hours prior to sacrifice (at 0800 hours). The amount of feed consumed by all groups was comparable to the control group. The following protocols were performed to yield the samples displayed in Table III:

entry 2: protocol I, followed by protocol IV entry 3: protocol III, followed by protocol IV entry 4: protocol III, followed by protocol IV entry 5: protocol IV entry 6: protocol IV All other samples were obtained from commercially available sources.

The results are displayed below in Table III. Percentages of increases or decreases are shown in parentheses.

respectively) were recorded, while the level of HDL-cholesterol decreased only slightly (10.8%). Decreases in triglycerides and glucose levels were also observed.

EXAMPLE 8

This example demonstrates that waxes (sterols) were not responsible for the cholesterol-lowering properties of Louisiana rice bran and its oil. Each group of 6 chickens (6-week old female while leghorn) was administered the chick mash diet described in Example 5, supplemented with one of three different amounts of waxes (sterols), 50 ppm of TRF (prepared as in Example 2) or 5% equivalent of the methanol insoluble fraction Louisiana rice bran oil. The amount of feed consumed by all groups was comparable to the control group and the feeding period was 4 weeks. The birds were fasted for a period of 14 hours prior to sacrifice (at 0800 hours). The following protocols were performed on the samples displayed in Table IV:

waxes (entries 2–4): Protocol VII.

TRF (entry 5) was obtained using the method described in Example 2. The methanol insoluble fraction (entry 6) was obtained by freezing Louisiana rice bran oil (prepared using protocols I and IV), then centrifuging. The resultant supernatant was extracted 3 times with twice the volume of methanol.

TABLE III

| Nutritional State[1] | SERUM CHOLESTEROL (mg/100/ml) | | | | |
|---|---|---|---|---|---|
| | Total Chol. | HDL-Chol. | LDL-Chol. | Triglycerides | Glucose |
| 1) Chick Diet + 5.0% Corn Oil (CDC) | $185 \pm 51^A$ $(100.0)^2$ | $110.3 \pm 4.95^A$ $(110.0)^2$ | $61.9 \pm 4.49^A$ $(100.0)^2$ | $90.2 \pm 2.17^A$ $(100.0)^2$ | $124.6 \pm 2.30^A$ $(100.0)^2$ |
| 2) Chick Diet + 5.0% Louisiana Rice Bran Oil (LRB0) | $129.7 \pm 4.1^B$ (70.7) | $99.8 \pm 3.57^A$ (90.5) | $27.9 \pm 2.60^B$ (45.1) | $84.5 \pm 2.97^A$ (93.7) | $117.3 \pm 5.92^{A,B}$ (94.1) |
| 3) Chick Diet + 5.0% Hot Extracted LRBO | $135.3 \pm 4.5^B$ (73.1) | $102.6 \pm 4.93^A$ (93.0) | $30.0 \pm 2.89^B$ (48.5) | $81.3 \pm 3.94^{B,C}$ (90.1) | $112.4 \pm 4.65^B$ (90.2) |
| 4) Chick Diet + 5.0% Cold Extracted LRBO | $121.6 \pm 3.5^C$ (65.7) | $98.4 \pm 4.99^A$ (89.2) | $26.1 \pm 2.89^B$ (42.2) | $77.4 \pm 4.81^C$ (85.6) | $113.2 \pm 4.40^B$ (90.9) |
| 5) Chick Diet + 5.0% Louisiana Crude Rice Bran Oil Unstabilized | $154.5 \pm 3.4^D$ (83.5) | $108.6 \pm 3.25^A$ C98.5) | $46.7 \pm 3.25^C$ (75.4) | $86.6 \pm 4.64^{A,B}$ (96.0) | $116.5 \pm 6.21^B$ (93.5) |
| 6) Chick Diet + 5.0% Commercial Rice Bran Oil | $163.3 \pm 5.3^E$ (88.2) | $102.4 \pm 4.10^A$ (92.8) | $55.8 \pm 3.84^D$ (90.1) | $88.5 \pm 4.53^A$ (98.1) | $116.2 \pm 4.78^B$ (93.3) |

[1]Feeding period was 4 weeks; time of killing was 0800 hours. The birds were fasted for 14 hours prior to killing. Data expressed as means ± SD; n = 6 chickens per group.
[2]Percentage of increases or decreases are in parentheses.
[A–E]Values not sharing a common superscript letter are different at $P < 0.01$.

The diet supplemented with 5% cold extracted Louisiana rice bran oil demonstrated superior cholesterol-lowering ability over the other diets. Impressive decreases in total serum and LDL-cholesterol (34.3% and 57.8%, All other samples were obtained from commercially available sources.

The results are displayed below in Table IV. Percentages of increases or decreases are shown in parentheses.

TABLE IV

| | | Serum Cholesterol (mg/100/ml) | | | HMG-CoA Reductase | Cholesterol 7a-Hydroxylase |
|---|---|---|---|---|---|---|
| Nutritional State[1] | | Total Chol. | HDL-Chol. | LDL-Chol. | (pmoles/mg/min)[2] | (moles/mg/min)[3] |
| 1) Chick Diet + 5.0% Corn Oil (CDCO) | | $185.1 \pm 4.12^A$ $(100.0)^4$ | $110.3 \pm 4.95^A$ $(100.0)^4$ | $61.9 \pm 1.49^A$ $(100.0)^4$ | $344.3 \pm 1.49^A$ $(100.0)^4$ | $0.855 \pm 0.084^A$ $(100.0)^4$ |
| 2) Chick Diet + 5.0% Corn Oil + Waxes; 50 ppm | | $184.7 \pm 6.50^A$ (99.8) | $109.6 \pm 2.83^A$ (99.4) | $61.7 \pm 1.71^A$ (99.7) | $339.3 \pm 19.7^A$ (98.5) | $0.837 \pm 0.081^A$ (97.9) |

TABLE IV-continued

| Nutritional State[1] | Serum Cholesterol (mg/100/ml) | | | HMG-CoA Reductase (pmoles/mg/min)[2] | Cholesterol 7a-Hydroxylase (moles/mg/min)[3] |
|---|---|---|---|---|---|
| | Total Chol. | HDL-Chol. | LDL-Chol. | | |
| 3) Chick Diet + 5.0% Corn Oil + Waxes; 5,000 ppm | 173.8 ± 7.31[A] (93.9) | 106.2 ± 4.69[A] (96.3) | 58.1 ± 1.77[A] (93.9) | 317.1 ± 14.4[A,B] (92.1) | 0.846 ± 0.072[A] (98.9) |
| 4) Chick Diet + 5.0% Corn Oil + Waxes; 10,000 ppm | 165.9 ± 4.90[B] (89.6) | 108.5 ± 4.68[A] (98.4) | 57.9 ± 1.48[A] (93.5) | 304.5 ± 14.4[B] (58.4) | 0.902 ± 0.080[A] (105.5) |
| 5) Chick Diet + 5.0% Corn Oil + Tocotrienol-Rich-Fraction; 50 ppm | 134.8 ± 3.82[C] (72.8) | 104.3 ± 3.99[A] (94.6) | 25.9 ± 1.02[B] (41.8) | 276.0 ± 17.4[C] (80.2) | 1.068 ± 0.047[B] (124.9) |
| 6) Chick Diet + 5.0% Methanol Insoluble Fraction | 180.2 ± 6.01[A] (97.4) | 104.0 ± 4.57[A] (94.3) | 62.6 ± 1.68[A] (101.1) | 321.1 ± 19.3[B] (93.3) | .852 ± 0.090[A] (99.6) |

[1]Feeding period was four weeks; time of killing was 0800 hours. The birds were fasted for 14 hours prior to killing. Data expressed as means ± SD; n = 6 chickens per group.
[2]p-moles of mevalonic acid synthesized per minute per mg of microsomal protein.
[3]n-moles of [$^{14}$c] 7-α-hydroxycholesterol per minute per mg of microsomal protein.
[4]Percentages of increases or decreases are in parentheses.
[A–D]Values not sharing a common superscript letter are different at $P < 0.01$.

The diets supplemented with sterols were not effective in lowering total serum or LDL-cholesterol levels. The maximum decrease in total cholesterol recorded with the sterol supplemented diet was 10.6% and that for LDL-cholesterol was only 6.5%. Only a marginal decrease was observed in hepatic enzymatic activity of HMG-CoA reductase (11.6%). Conversely, chickens fed the diet supplemented with the methanol soluble fraction of the TRF recorded a substantial decrease in the levels of total serum cholesterol (27.2%), LDL-cholesterol (58.2%) and hepatic enzymatic activity of HMG-CoA reductase (19.8%). Therefore, the methanol soluble fraction of the TRF (containing the tocotrienols according to this invention), rather than sterols, was responsible for the impressive cholesterol-reducing properties of rice bran oil.

EXAMPLE 9

This study was conducted to determine if sterols were responsible for the reduction in serum levels of various enzymes and blood constituents observed with rice bran. The feeding conditions described in Example 8 were used. The samples were prepared as described in Example 8.

The results are displayed below in Table V. Percentages of increases or decreases are shown in parentheses.

TABLE V

| Nutrional State[1] | Fatty Acid Synthetase[2] (pmoles/mg/min) | Triglycerides (mg/100 ml) | Glucose (mg/100 ml) | Thromboxane B$_2$ (mg/100 ml) | Platelet Factor 4 (ng/ml) |
|---|---|---|---|---|---|
| 1) Chick Diet + 5.0% Corn Oil (CDCO) | 61.4 ± 2.4[A] (100.0)[3] | 90.2 ± 1.17[A] (100.0)[3] | 124.6 ± 2.3[A] (100.0)[3] | 16.7 ± 1.69[A] (100.0)[3] | 7.2 ± 0.48[A] (100.0)[3] |
| 2) Chick Diet + 5.0% Corn Oil + Waxes; 50 ppm | 62.5 ± 1.9[A] (102.0)[3] | 91.5 ± 1.48[A] (101.4)[3] | 126.7 ± 2.1[A] (101.7)[3] | 15.8 ± 1.29[A] (94.6)[3] | 7.5 ± 0.42[A] (104.2)[3] |
| 3) Chick Diet + 5.0% Corn Oil + Waxes; 5,000 ppm | 63.6 ± 2.8[B] (103.8)[3] | 95.2 ± 1.01[A] (105.5)[3] | 123.9 ± 1.52[A] (99.4)[3] | 16.4 ± 1.66[A] (98.2)[3] | 7.4 ± 0.36[A] (102.8)[3] |
| 4) Chick Diet + 5.0% Corn Oil + Waxes; 10,000 ppm | 60.4 ± 1.9[A] (98.5)[3] | 96.1 ± 1.90[A] (106.5)[3] | 124.3 ± 1.18[A] (99.8)[3] | 16.8 ± 1.67[A] (100.6)[3] | 7.4 ± 0.87[A] (102.8)[3] |
| 5) Chick Diet + 5.0% Corn Oil + Tocotrienol-Rich-Fraction; 50 ppm | 68.5 ± 2.1[B] (111.7)[3] | 73.2 ± 1.69[B] (81.2)[3] | 86.4 ± 1.55[B] (69.3)[3] | 12.4 ± 1.42[B] (74.3)[3] | 5.7 ± 0.64[B] (79.2)[3] |
| 6) Chick Diet + 5.0% Methanol Insoluble Fraction | 65.8 ± 1.2[B] (107.3) | 89.5 ± 1.21[A] (99.2) | 111.1 ± 2.45[C] (89.4)[3] | 15.41 ± 1.64[A] (92.2)[3] | 7.5 ± 0.36[A] (104.2) |

[1]Feeding period was four weeks; time of killing was 0800 hours. The birds were fasted for 14 hours prior to killing. Data expressed as means ± SD; n = 6 chickens per group.
[2]n-moles of NADPH oxidized per minute per mg of cytosolic protein.
[3]Percentages of increases or decreases are in parentheses.
[A–C]Values not sharing a common superscript letter are different at $P < 0.01$.

These results show that the sterols are not responsible for the reduction in the levels of triglycerides, glucose, thromboxane B$_2$ or platelet factor 4 levels observed with rice bran and its oil. In fact, the sterols either increased or had no significant effect on the level of each of those factors.

Conversely, the chickens fed with the diet supplemented with the methanol soluble fraction of the TRF of Louisiana rice bran induced significant decreases in all of these factors.

EXAMPLE 10

This study measured the effects of three tocotrienols isolated from rice bran on cholesterol-related enzyme activity in hepatocytes isolated from livers of 8-week old female chickens. The chickens were fed the chick mash diet for 8 weeks. They were then fasted for 40 hours and finally refed for 48 hours before sacrifice. The hepatocytes were then prepared following standard methods.

Each compound was isolated from TRF using the following protocol: A bond Elute amine column was equilibrated with 2 ml hexane. 10 mg of TRF (dissolved in 0.5 ml hexane) was bound to the amine column. The column was washed with 1 ml of hexane, then with 1 ml of 3% isopropanol in hexane. P-21 and P-25 were eluted off the column with 5% isopropanol in hexane. Then using 10% isopropanol in hexane, the impurity P-20 was eluted. α-tocotrienol was also tested.

The results are displayed below in Table VI. Percentages of increases or decreases are shown in parentheses.

TABLE VI

| Concentration in[1] (μg/mL) | HMG-CoA Reductase pmoles/min/mg | Fatty Acid Synthase nmoles/min/mg | Cholesterol 7α-hydroxylase pmoles/min/mg |
|---|---|---|---|
| A) α-Tocotrienol | | | |
| 1.   0.0 | 26.8 (100.0) | 17.2 (100.0) | 2.31 (100.0) |
| 2.  10.0 | 21.4 (79.9) | 15.2 (88.4) | 2.12 (91.8) |
| 3.  20.0 | 17.3 (64.6) | 14.3 (83.2) | 2.27 (98.7) |
| 4.  40.0 | 16.7 (62.3) | 12.4 (72.1) | 2.34 (101.3) |
| B) P-21 (Tocotrienol) | | | |
| 1.   0.0 | 26.8 (100.0) | 17.2 (100.0) | 2.31 (100.0) |
| 2.  10.0 | 29.4 (76.0) | 14.3 (83.1) | 2.41 (104.3) |
| 3.  20.0 | 16.7 (62.3) | 12.7 (73.8) | 3.40 (103.9) |
| 4.  40.0 | 14.2 (52.9) | 11.8 (68.6) | 2.39 (103.5) |
| 5.  80.0 | 14.3 (53.4) | 10.2 (59.3) | 1.37 (102.6) |
| C) P-25 | | | |
| 1.   0.0 | 26.8 (100.0) | 17.2 (100.0) | 2.31 (100.0) |
| 2.  10.0 | 19.0 (70.9) | 16.2 (94.2) | 2.33 (100.9) |
| 3.  20.0 | 15.3 (57.1) | 14.3 (83.1) | 2.37 (102.61) |
| 4.  40.0 | 12.4 (46.3) | 12.7 (73.8) | 2.44 (105.6) |
| 5.  80.0 | 11.1 (41.4) | 12.1 (70.3) | 2.37 (102.6) |
| D) P-20 | | | |
| 1.   0.0 | 28.78 (100.0) | | |
| 2.  25.0 | 29.21 (101.5) | | |
| 3.  55.0 | 28.87 (100.3) | | |
| 4. 100.0 | 28.21 (98.0) | | |

[1]Feeding period was 8 weeks; the birds were fasted for 40 hrs. and refed for 48 hrs. The hepatocytes were prepared at 10 PM from two livers by standard methods.

$P_{25}$ demonstrated very effective dose dependant inhibition of HMG-CoA reductase with maximum reductions in activity of 46.6% and 58.6%, respectively. In fact, $P_{25}$ exerted substantially better effects than the known hypercholesterolemic agent, α-tocotrienol. α-tocotrienol showed a maximum reduction of only 37.7%. $P_{20}$, the sterol contaminant, showed no significant effect on the activity of HMG-CoA reductase.

EXAMPLE 11

We next measured the effects of various tocotrienols and tocotrienol-like compounds isolated from rice bran on the activity of HMG-CoA reductase. 20.0 g of stabilized rice bran was extracted with 200.0 ml of methanol to remove various UV absorbing impurities and tocotrienols (6.7 mg total). This step was repeated four times. The remaining residue was dried under vacuum in a desiccator and then heated at 180° C. for 2 hours under 30 psi pressure. Then the dried residue was extracted again with 200.0 ml methanol (3.4 mg). The various peaks were purified by HPLC except 100 μl was injected instead of 20 μl. Twenty runs were done to obtain enough material for this study. The peaks which eluted at 32, 36, 45 and 54 minutes were tested in chicken hepatocytes as in Example 10.

The results of the HMG-CoA reductase assay are displayed below in Table VII.

TABLE VII

| Concentration[1] | HMG-CoA Reductase (pmoles/min/mg of microsome) | | | |
|---|---|---|---|---|
| (μg/ml) | P-32 | P-36 | P-45 | P-54 |
| 1)  0.00 | 28.78 | 28.78 | 28.78 | 28.78 |
| 2) 10.00 | 24.67 | 23.78 | 22.61 | 25.46 |
| 3) 20.00 | 21.31 | 20.12 | 20.33 | 19.67 |
| 4) 30.00 | 18.36 | 17.24 | 19.67 | 20.11 |
| 5) 40.00 | 16.59 | 17.34 | 18.21 | 18.19 |
| 6) 50.00 | 16.61 | 15.21 | 18.40 | 18.20 |

[1]Feeding period was 8 weeks; the birds were fasted for 40 hrs. and refed for 48 hrs.
The hepatocytes were prepared at 10 PM from two livers by standard methods.

Each of these compounds demonstrated an ability to inhibit the activity of HMG-CoA reductase. Most notably, $P_{36}$ showed a 47% maximum reduction of activity.

EXAMPLE 12

This example measured the effects of the TRF and its components on the hepatic enzymatic activity of HMG-CoA reductase and cholesterol 7α-hydroxylase. Each group of 12 chickens (6-week old female white leghorn) was administered either a control diet or a control diet supplemented with the TRF, a component of the TRF a commercial cholesterol inhibitor (either Lovastatin or Geraniol) or a combination of the commercial inhibitors. The amount of feed consumed ranged from 11.19–11.60 g per chicken and the feeding period was 4 weeks. The birds were fasted for a period of 36 hours and refed for 48 hours prior to sacrifice (at 0800 hours).

The TRF (entry 2) was prepared as described in Example 10. Geraniol was obtained from Sigma Chemical Co. and Lovastatin was obtained under the brand name LOVOCOR.

The chicken diet for this study contained the following ingredients:

| Ingredients | Percentage |
|---|---|
| Corn (9.3% protein) | 61.5 |
| Soybean Meal (44.0% protein) | 30.0 |
| Meat scrap (50.0% protein) | 5.0 |
| Calcium Carbonate | 0.5 |
| Dicalcium phosphate | 1.0 |
| Alfalfa (17% protein) | 1.0 |

-continued

| Ingredients | Percentage |
|---|---|
| Mineral Mixture[a] | 0.5 |
| Vitamin Mixture[b] | 0.5 |

[a]Mineral mixture contained per kg feed: zinc sulfate, 50 mg; sodium chloride, 2.0 mg; and manganese dioxide, 50.0 mg.
[b]Vitamin mixture contained per kg feed: vitamin A, 2,000 units; vitamin $D_3$, 200 units; vitamin E, 10 units, riboflavin, 3.6 mg; vitamin $B_{12}$, 0.01 mg; and vitamin $K_1$, 0.50 mg.

The results are displayed below in Table VIII. Percentages of increases or decreases are in parentheses.

TABLE VIII

| Nutritianol State[1] | HMG-CoA Reductase[2] pmole/min./mg | Cholesterol 7α-Hydroxylase[3] nmole/min./mg |
|---|---|---|
| 1) Control Diet (CD) | 513.25 ± 15.07[A] (100.00)[4] | 10.22 ± 0.25[A] (100.00)[4] |
| 2) CD + TRF-RBO; 50 ppm | 441.14 ± 7.28[B] (85.95)[4] | 10.80 ± 0.18[A] (105.00)[4] |
| 3) CD + α – $T_3$; 50 ppm | 459.02 ± 1505[B] (89.43)[4] | 10.69 ± 0.20[A] (104.60)[4] |
| 4) CD + γ – $T_3$; 50 ppm | 401.99 ± 5.84[C] (78.32)[4] | 10.97 ± 0.17[A] (107.34)[4] |
| 5) CD + δ – $T_3$; 50 ppm | 389.22 ± 8.54[C] (75.83)[4] | 10.98 ± 0.16[A] (107.44)[4] |
| 6) CD + P-21-$T_3$; 50 ppm | 373.78 ± 7.99[D] (72.83)[4] | 11.49 ± 0.20[B] (112.43)[4] |
| 7) CD + P-25-$T_3$; 50 ppm | 366.10 ± 6.66[D] (71.33)[4] | 11.39 ± 0.26[B] (111.45)[4] |
| 8) CD + Geraniol; 100 ppm | 449.89 ± 12.82[B] (87.65)[4] | 10.28 ± 0.27[A] (100.59)[4] |
| 9) CD + Lovastatin; 100 ppm | 527.11 ± 13.93[A] (102.69)[4] | 11.34 ± 0.31[B] (110.96)[4] |
| 10) CD + Geraniol + Lovastatin 50 ppm + 50 ppm | 442.48 ± 1.64[B] (86.21)[4] | 11.24 ± 0.17[B] (109.98)[4] |

[1]Feeding period was 4 weeks. Time of sacrificing was 0800 hr. The birds were fasted for 36 hrs. and refed 48 hrs. at the end of feeding period (28 days), and then sacrificed. Data expressed as means ± SD; n = 12 birds per group.
[2]pmoles of HMG-CoA formed per minute per mg of microsomal protein.
[3]nmoles of [$^{14}$c]-cholesterol into [$^{14}$-c] 7-α-hydroxycholeterol per minute per mg of microsomal protein.
[4]Percentages of increases are in parentheses.
[A–D]Values not sharing a common superscript letter are different at P < 0.01.

$P_{25}$ was the best inhibitor of HMG-CoA reductase. The enzymatic activity of HMG-CoA reductase was reduced by about 28% with $P_{25}$, while twice the amount of the commercial cholesterol-lowering drugs provided a maximum reduction of only about 13%. These data indicate that the fused oxygen heterocycle of the tocotrienols increases the biological activity as compared with a single ring system, such as Geraniol. We believe that a three ring system might provide additional activity. Alternatively, adding substituents such as carbonyls, hydroxyls and alkyls may also enhance the biological activity of tocotrienol-like compounds.

EXAMPLE 13

We next studied the effects of the TRF and its components on total serum cholesterol levels, the HDL-cholesterol/total cholesterol ratio and the HDL-/LDL-cholesterol ratio. Feeding conditions were identical to those in Example 12.

The samples were prepared as described in Example 12.

The results are displayed below in Table IX. Percentages of increases or decreases are in parentheses.

TABLE IX

| NUTRITIONAL STATE[1] | Concentration in serum (mg/dl) | | | | |
|---|---|---|---|---|---|
| | Total Cholesterol | HDL-Cholesterol | LDL-Cholesterol | DL-Cholesterol/ Total Cholesterol | HDL-Cholesterol/ LDL-Cholesterol |
| 1) Control Diet (CD) | 142.77 ± 1.916[A] (100.00)[2] | 83.66 ± 0.85[A] (100.00)[2] | 55.06 ± 0.89[A] (100.00)[2] | 0.59 (100.00)[2] | 1.52 (100.00)[2] |
| 2) CD + TRF-RBO 50 ppm | 125.10 ± 1.50[B] (87.62) | 78.71 ± 1.06[B] (94.08) | 43.47 ± 0.78[B] (78.95) | 0.63 (102.40) | 1.81 (119.20) |
| 3) CD + α – $T_3$ 50 ppm | 131.71 ± 1.08[C] (92.25) | 80.47 ± 0.67[B] (96.19) | 47.97 ± 0.56[C] (87.12) | 0.61 (104.30) | 2.09 (110.40) |
| 4) CD + γ – $T_3$ 50 ppm | 116.86 ± 1.47[D] (81.85) | 78.39 ± 0.96[B] (93.70) | 37.52 ± 0.81[D] (68.14) | 0.67 (114.50) | 2.09 (137.50) |
| 5) CD + δ – $T_3$ 50 ppm | 119.40 ± 1.41[D] (83.63) | 77.78 ± 0.97[B] (93.08) | 36.14 ± 0.97[D] (65.64) | 0.65 (111.30) | 2.15 (141.80) |
| 6) CD + P-21-$T_3$ 50 ppm | 92.91 ± 1.27[E] (65.08) | 68.88 ± 1.52[C] (82.33) | 22.16 ± 0.57[E] (40.25) | 0.74 (126.50) | 3.11 (204.60) |
| 7) CD + P-25-$T_3$ 50 ppm | 95.51 ± 1.11[E] (66.90) | 70.12 ± 1.25[C] (53.82) | 23.00 ± 1.27[E] (41.77) | 0.73 (125.30) | 3.05 (200.60) |
| 8) CD + Geraniol 100 ppm | 122.53 ± 1.37[D] (85.82) | 82.28 ± 1.06[A] (98.35) | 41.07 ± 1.13[F] (96.30) | 0.65 (110.10) | 2.00 (131.50) |
| 9) CD + Lovastatin 100 ppm | 128.65 ± 1.02[C] (90.11) | 81.38 ± 0.73[A] (97.28) | 44.12 ± 1.26[B] (86.51) | 0.63 (108.00) | 1.84 (121.40) |
| 10) CD + Geraniol + Lovastatin; 50 ppm + 50 ppm | 119.92 ± 0.91[D] (84.00) | 80.93 ± 0.62[B] (96.74) | 41.31 ± 1.13[B] (89.29) | 0.67 (115.20) | 1.96 (128.90) |

[1]Feeding period was 4 weeks. Time of drawing the blood was 0800 hr. Data expressed as means ± SD; n = 12 birds per group.
[2]Percentages of increases or decreases are in parentheses.
[A–F]Values not sharing common superscript letter re different P < 0.01.

$P_{21}$ and $P_{25}$ decreased the levels of serum cholesterol to a substantially greater degree than any other compound tested, including Lovastatin and Geraniol. $P_{25}$ caused about a 33% reduction. In comparison, Geraniol effected a 14% reduction and Lovastatin caused only a 10% reduction. $P_{21}$ and $P_{25}$ were also clearly superior than the other compounds in increasing the HDL-/LDL-cholesterol ratio. Both of these compounds induced over a 100% increase in the HDL-/LDL-cholesterol ratio, while Lovastatin and Geraniol increased the ratio by a maximum of 31.5%.

EXAMPLE 14

We next measured the effects of TRF and its components on serum levels of apolipoprotein $(a)_1$, apolipoprotein B, triglycerides and glucose and the plasma levels of thromboxane $B_2$ and platelet factor 4. Feeding conditions were identical to Example 12.

The samples were prepared as described in Example 12.

The results are displayed below in Table X. Percentages of increases or decreases are in parentheses.

EXAMPLE 15

We next measured the effects of various tocotrienols from rice bran on HMG-CoA reductase and cholesterol 7α-hydroxylase in hypercholesterolemic swine. Since pigs are very similar to humans in their cholesterol metabolism, they provide a useful model from which to study hypercholesterolemia and related diseases. The pigs used in this study carried $Lpd^5$ and $Lpu^1$ mutant alleles for apolipoprotein B and U. Because of this genetic defect, these pigs demonstrate spontaneously elevated LDL-cholesterol levels and hypercholesterolemia. The serum cholesterol concentration in these swine is typically above 300–500 mg/dl, as compared to 120–160 mg/dl in normal adult swine. As a result, the pigs develop complicated atherosclerotic plaques that closely resemble advanced atherosclerotic lesions found in humans.

Each group of three 5-month old swine was administered either a control diet or a control diet supplemented with 50 ppm of TRF or 50 ppm of an individual tocotrienol. The samples were prepared as described in Example 11. After a 12 hour fast, serum and plasma samples were taken a 0 hrs, 21 days and 42 days from the start of the feeding period.

TABLE X

| Nutritional State[1] | Concentration In Serum (mg/100 ml) | | | | Thromboxane $B_2$ (pg/ml) | Platelet Factor 4 (ng/ml) |
| --- | --- | --- | --- | --- | --- | --- |
| | APO $A_1$ | APO B | Triglycerides | Glucose | | |
| 1) Control diet (CD) | 140.40 ± 1.7[A] (100.00)[2] | 33.10 ± 0.28[A] (100.00)[2] | 74.03 ± 1.26[A] (100:00)[2] | 224.30 ± 5.30[A] (100:00)[2] | 25.84 ± 0.84[A] (100.00)[2] | 13.09 ± 0.49[A] (100.00)[2] |
| 2) CD + TRF-RBO; 50 ppm | 140.2 ± .8[B] (99.86) | 28.90 ± 0.28[B] (87.31) | 64.73 ± 0.93[B] (87.44) | 212.50 ± 0.98[B] (94.74) | 20.55 ± 0.95[B] (79.53) | 9.67 ± 0.43[B] (73.87) |
| 3) CD + α – $T_3$; 50 ppm | 139.6 ± 3.2[A] (99.43) | 29.30 ± 0.16[B] (88.52) | 68.04 ± 1.32[C] (91.91) | 216.90 ± 1.62[B] (96.70) | 21.63 ± 0.89[B] (83.71) | 8.78 ± .0.72[C] (67.07) |
| 4) CD + γ – $T_3$; 50 ppm | 139.80 ± 1.5[A] (99.57) | 29.53 ± 3.47[B] (89.21) | 61.07 ± 1.37[D] (82.49) | 208.70 ± 1.41[C] (93.05) | 19.22 ± 0.78[B,C] (74.38) | 8.36 ± 0.79[C] (63.87) |
| 5) CD + δ – $T_3$; 50 ppm | 139.30 ± 1.4[A] (99.22) | 27.30 ± 0.28[B] (82.48) | 60.50 ± 2.50[D] (81.72) | 205.30 ± 1.83[C] (91.53) | 18.65 ± 0.99[C] (72.17) | 8.23 ± 0.77[C] (62.87) |
| 6) CD + P-21-$T_3$; 50 ppm | 138.4 ± 4.4[A] (98.79) | 25.40 ± 0.40[C] (76.74) | 56.22 ± 1.11[E] (75.94) | 198.80 ± 2.10[D] (88.63) | 16.74 ± 1.62[C] (64.78) | 7.76 ± 1.67[C] (59.28) |
| 7) CD + P-25-$T_3$; 50 ppm | 138.70 ± 2.7[A] (98.78) | 25.20 ± 0.40[C] (76.13) | 54.65 ± 1.42[E] (73.82) | 196.10 ± 1.74[D] (87.43) | 16.42 ± 1.36[C] (63.54) | 7.27 ± 0.74[C] (55.54) |
| 8) CD + Geraniol; 100 ppm | 138.40 ± 1.7[A] (98.58) | 29.20 ± 0.45[B] (88.22) | 71.29 ± 1.19[F] (96.30) | 227.60 ± 2.03[A] (101.47) | 25.46 ± 1.52[A] (98.53) | 12.38 ± 1.26[B] (94.57) |
| 9) CD + Lovastatin; 100 ppm | 139.9 ± 1.4[D] (99.29) | 25.80 ± 0.89[C] (77.95) | 64.04 ± 1.03[B] (86.51) | 220.10 ± 1.32[D] (98.13) | 24.89 ± 0.88[A] (96.32) | 12.24 ± 1.49[B] (93.51) |
| 10) CD + Geraniol + Lovastatin; 50 ppm + 50 ppm | 139.6 ± 4.8[A] (99.43) | 25.95 ± 0.34[C] (78.40) | 66.10 ± 0.99[B] (89.29) | 221.70 ± 1.89[D] (98.84) | 24.95 ± 0.97[A] (96.56) | 12.19 ± 1.15[B] (93.12) |

[1]Feeding period was 4 weeks. Time of drawing the blood was 0800 hr. Data expressed as means ± SD; n = 12 birds per group.
[2]Percentages of increases or decreases are in parentheses.
[A–F]Values not sharing common superscript letter re different P < 0.01.

$P_{21}$ and $P_{25}$ were the most potent cholesterol inhibitors. They effected the highest Apo $A_1$ to Apo B ratio and resulted in the maximum decrease in serum levels of triglycerides and glucose. In addition, they also reduced plasma levels of thromboxane $B_2$ and platelet factor 4 to a greater extent than any other compound tested.

After taking serum and plasma samples from the pigs at the end of the 42 day period, all of the swine were fasted for a total of 40 hours, followed by a 48 hour refeeding period. One swine from each group was sacrificed at that time and the liver, intestine, lung, heart, loin muscle, adipose tissue and ham muscle were removed.

The swine diet contained the following ingredients:

| Ingredients | Percentage |
|---|---|
| Corn (9.3% protein) | 78.37 |
| Soybean Meal (44.0% protein) | 15.42 |
| Lard | 3.00 |
| Calcium Carbonate | 0.95 |
| Dicalcium Phosphate | 0.96 |
| Mineral Mixture[a] | 0.30 |
| Vitamin Mixture[b] | 1.00 |

[a]Mineral mixture contained per kg feed: zinc sulfate $H_2O$, 110 mg; manganese sulfate $5H_2O$, 70 mg; ferric citrate $H_2O$, 500.0 mg; copper sulfate $5H_2O$, 16.0 mg; sodium selenite, 0.2 mg; DL-methionine, 2.5 g; choline chloride (50%), 1.5 g; ethoxyquin (1,2-dihydro-6-ethoxy-2,2,4-trimethyl-quinoline), 125 mg; and thiamine-HCl, 1.8 mg.
[b]Vitamin mixture contained per kg feed: vitamin A, 1,500 units; vitamin $D_3$, 400 units; vitamin E, 10 units, riboflavin, 3.6 mg; calcium pantothenate, 10.0 mg; niacin, 25.6 mg; pyridoxine-HCl, 3.0 mg; folacin, 0.55 mg; biotin, 0.15 mg; vitamin $B_{12}$, 0.01 mg; and vitamin $K_1$, 0.55 mg.

The gain in body weight in all groups was comparable to the control, although feed conversion efficiency increased 7% with $P_{21}$ and 10% with $P_{25}$.

The results of this study are displayed in Table XI. Percentages of increases and decreases are shown in parentheses.

TABLE XI

HMG-CoA REDUCTASE[2] pg/min/mg of microsomes

| NUTRITIONAL STATE[1] | Experimental Diets Feeding Period | | | Percentage of Control Activity |
|---|---|---|---|---|
| | 0-Time | 21 days | 42 days | |
| Hypercholesterolemic Swine | 355.49 ± 8.44 | 374.14 ± 13.35 | 391.38 ± 15.75 | |
| 2) Control Diet (CD) | (100.00) | (105.25) | (110.09) | 100.00[A] |
| 3) CD + TRF RB-oil; 50 ppm | 348.92 ± 10.62 | 300.72 ± 10.53 | 285.13 ± 15.58 | |
| | (100.00) | (86.19) | (81.72) | 74.23[A] |
| 4) CD + γT$_3$; 50 ppm | 347.99 ± 16.29 | 300.72 ± 10.53 | 280.88 ± 12.81 | |
| | (100.00) | (86.19) | (80.71) | 73.31[B] |
| 5) CD + P-21-T$_3$; 50 ppm | 340.36 ± +23.55 | 304.23 ± 23.13 | 275.75 ± 12.76 | |
| | (100.00) | (89.38) | (81.02) | 73.59[B] |
| 6) CD + P-25-T$_3$; 50 ppm | 350.86 ± 23.79 | 307.27 ± 23.36 | 269.43 ± 13.23 | |
| | (100.00) | (87.58) | (76.79) | 69.75[B] |

[1]Corn-soybean meal control diet or experimental diets were fed to 5-month-old swine for 42 days. Then all groups were fasted for 40 hrs. and refed for 48 days. The time of sacrificing was 9:00 a.m. All tissues were kept on ice. TRF = Tocotrienol-Rich-Fraction.
[2]Data expressed as means ± SD; n = 6 samples of 3 swine per group;
[A-B]Values not sharing a common superscript letter are different at $P < 0.01$.

CHOLESTEROL 7α-HYDROXYLASE[2] pg/min/mg of microsomes

| NUTRITIONAL STATE[1] | Experimental Diets Feeding Period | | | Percentage of Control Activity |
|---|---|---|---|---|
| | 0-Time | 21 days | 42 days | |
| Hypercholesterolemic Swine | 4.88 ± 0.75 | 5.00 ± 0.60 | 5.07 ± 0.61 | |
| | (100.00)[A] | (102.46)[3] | (103.89)[3] | 100.00[A] |
| 2) Control Diet (CD) | | | | |
| 3) CD + TRF RB-oil; 50 ppm | 4.58 ± 0.10 | 4.96 ± 0.13 | 5.02 ± 0.11 | |
| | (100.00) | (108.29) | (109.61) | 105.50[A] |
| 4) CD + γ- T$_3$; 50 ppm | 4.49 ± 0.13 | 4.53 ± 0.12 | 4.58 ± 0.19 | |
| | (100.00) | (100.89) | (102.00) | 98.18[A] |
| 5) CD + Desmethyl-T$_3$; (P-21); 50 ppm | 4.53 ± 0.10 | 4.50 ± 0.18 | 4.63 ± 0.56 | |
| | (100.00) | (99.34) | (102.21) | 98.38[A] |
| 6) CD + Didesmethyl-T$_3$; (P-25); 50 ppm | 4.57 ± 0.19 | 4.62 ± 0.19 | 4.68 ± 0.18 | |
| | (100.00) | (101.09) | (102.41) | 98.58[A] |

[1]Corn-soybean meal control diet or experimental diets were fed to 5-month-old swine for 42 days. Then all groups were fasted for 40 hrs. and refed for 48 days. The time of sacrificing was 9:00 a.m. All tissues were kept on ice. TRF = Tocotrienol-Rich-Fraction.
[2]Data expressed as means ± SD; n = 6 samples of 3 swine per group;
[3]Percentages of increases or decreases in respect to baseline value.
[A-B]Values not sharing a common superscript letter are different at $P < 0.01$.

The hepatic enzymatic activity of the HMG-CoA reductase decreased approximately 30% with all the tocotrienols tested. In addition, there was no significant decrease in the activity of cholesterol 7α-hydroxylase. These results were all time dependent and point to an overall reduction in cholesterogenesis, with no increase in cholesterol biosynthesis.

EXAMPLE 16

Further tests were conducted on the swine described in Example 16. The experimental conditions were the same, except that the two remaining swine in each group were transferred to the unsupplemented control diet following the 42 day feeding period. After an additional 70 days, serum and plasma samples were collected from these swine after a 12 hour fast for testing.

The samples were prepared as described in Example 12.

The results of these studies are displayed below in Tables XII–XV. Percentages of increases and decreases are shown in parentheses.

TABLE XII

TOTAL CHOLESTEROL CONCENTRATION IN SERUM (mg/100 ml)[2]

| NUTRITIONAL STATE[1] | Experimental Diets Feeding Period | | | Percentage of Control Activity | Control Diet Feeding Period | Percentage of Control Activity |
|---|---|---|---|---|---|---|
| | 0-Time | 21 days | 42 days | | 70 days | |
| Normolipemic Swine 1) Control Diet CCD) | 116.53 ± 5.64 (100:00)[3] | 131.83 ± 6.64 (113.13)[3] | 142.50 ± 2.75 (122.29)[3] | — | 147.20 ± 4.45 (126.32)[3] | — |
| Hypercholesterolemic Swine 2) Control Diet (CD) | 228.63 ± 21.89 (100.00) | 251.07 ± 16.82 (110.02) | 356.87 ± 8.69 (156.79) | 100.00[A] | 374.36 ± 13.50 (164.60) | 100.00[A] |
| 3) CD + TRF RD-oil; 50 ppm | 206.43 ± 18.45 (100.00) | 222.00 ± 15.75 (107.39) | 243.03 ± 12.28 (117.72) | 75.00[B] | 285.77 ± 14.00 (139.16) | 84.60[B] |
| 4) CD + γT$_3$; 50 ppm | 209.73 ± 8.50 (100.00) | 225.20 ± 8.36 (107.39) | 233.93 ± 5.35 (111.76) | 71.00[B] | 271.70 ± 6.84 (129.66) | 78.80[B] |
| 5) CD + P-21-T$_3$; 50 ppm | 220.50 ± 16.54 (100.00) | 236.40 ± 18.17 (107.20) | 238.17 ± 14.29 (108.20) | 68.90[B] | 276.23 ± 15.93 (125.39) | 76.20[B] |
| 6) CD + P-25-T$_3$; 50 ppm | 216.20 ± 12.50 (100.00) | 229.90 ± 13.97 (106.33) | 237.64 ± 12.15 (107.60) | 68.60[B] | 268.90 ± 11.41 (124.45) | 75.60[B] |

[1]Feeding period was 6 weeks. Time of drawing the blood was 0.009 hr. after fasted for 12 hrs; TRF = Tocotrienol-Rich-Fraction.
[2]Data expressed as means ± SD; n = 6 samples of 3 swine per group.
[3]Percentages of increases or decreases in respect to baseline value.
[A-B]Values not sharing a common superscript letter are different at $P < 0.01$.

TABLE XIII

HDL-CHOLESTEROL CONCENTRATION IN SERUM (mg/100 ml)[2]

| NUTRITIONAL STATE[1] | Experimental Diets Feeding Period | | | Percentage of Control Activity | Control Diet Feeding Period | Percentage of Control Activity |
|---|---|---|---|---|---|---|
| | 0-Time | 21 days | 42 days | | 70 days | |
| Normolipemic Swine 1) Control Diet (CD) | 20.76 ± 0.67 (100.00)[3] | 23.63 ± 0.62 (113.82)[3] | 28.41 ± 1.67 (136.85)[3] | — | 29.78 ± 1.43 (143.45.)[3] | — |
| Hypercholesterolemic Swine 2) Control Diet (CD) | 24.04 ± 1.53 (100.00) | 25.82 ± 0.86 (107.40) | 28.27 ± 0.69 (117.59) | 100.00[A] | 31.42 ± 1.67 (130.69) | 100.00[A] |
| 3) CD + TRF RD-oil; 50 ppm | 23.36 ± 1.35 (100.00) | 25.14 ± 1.49 (107.62) | 26.50 ± 1.54 (113.44) | 96.47[A] | 30.19 ± 1.21 (129.24) | 98.89[A] |
| 4) CD + γT$_3$; 50 ppm | 21.86 ± 1.67 (100.00) | 25.27 ± 1.62 (115.59) | 28.55 ± 1.62 (130.60) | 111.06[B] | 30.47 ± 1.62 (139.39) | 106.66[A] |
| 5) CD+ P-21-T$_3$; 50 ppm | 22.95 ± 1.73 (100.00) | 26.23 ± 0.89 (114.29) | 30.74 ± 1.13 (133.94) | 113.90[B] | 31.15 ± 1.73 (135.72) | 103.50[A] |
| 6) CD + P-25-T$_3$; 50 ppm | 21.86 ± 0.99 (100.00) | 25.68 ± 1.67 (117.47) | 31.81 ± 1.75 (145.52) | 123.75[B] | 32.65 ± 1.09 (149.36) | 114.29[A] |

[1]Feeding period was 6 weeks. Time of drawing the blood was 0.009 hr. after fasting for 12 hrs.
[2]Data expressed as means ± SD; n = 6 samples of 3 swine per group; TRF = Tocotrienol-Rich-Fraction.
[3]Percentages of increases or decreases in respect to baseline value.
[A-B]Values not sharing a common superscript letter are different at $P < 0.01$.

TABLE XIV

LDL-CHOLESTEROL CONCENTRATION IN SERUM (mg/100 ml)[2]

| NUTRITIONAL STATE[1] | Experimental Diets Feeding Period | | | Percentage of Control Activity | Control Diet Feeding Period | Percentage of Control Activity |
|---|---|---|---|---|---|---|
| | 0-Time | 21 days | 42 days | | 70 days | |
| Normolipemic Swine | 92.84 ± | 107.31 ± | 110.88 ± | | 115.70 ± | |
| 1) Control Diet (CD) | 1.01 | 1.22 | 9.66 | | 11.69 | |
| | (100.00)[3] | (115.58)[3] | (119.43)[3] | — | (124.62)[3] | — |
| Hypercholesterolemic | 192.84 ± | 216.39 ± | 319.39 ± | | 274.11 ± | |
| Swine | 11.89 | 13.46 | 6.02 | | 13.55 | |
| 2) Control Diet (CD) | (100.00) | (112.21) | (164.07) | 100.00[A] | (142.14) | 100.00[A] |
| 3) CD + TRF RD-oil; | 177.28 ± | 187.15 ± | 209.09 ± | | 267.08 ± | |
| 50 ppm | 10.97 | 13.49 | 11.86 | | 7.7 | |
| | (100.00) | (105.57) | (117.94) | 71.88[B] | (150.65) | 105.99[A] |
| 4) CD + γT$_3$; 50 ppm | 178.37 ± | 185.12 ± | 193.80 ± | | 224.66 ± | |
| | 6.32 | 6.63 | 2.70 | | 3.71 | |
| | (100.00) | (103.78) | (108.65) | 66.22[C] | (125.95) | 88.61[B] |
| 5) CD + P-21-T$_3$; 50 ppm | 182.09 ± | 194.17 ± | 198.76 ± | | 227.82 ± | |
| | 14.03 | 11.74 | 9.57 | | 11.33 | |
| | (100.00) | (106.63) | (109.15) | 66.53[C] | (125.11) | 88.02[B] |
| 6) CD + P-25-T$_3$; 50 ppm | 182.37 ± | 191.05 ± | 198.01 ± | | 233.75 ± | |
| | 11.92 | 8.78 | 6.04 | | 7.49 | |
| | (100.00) | (104.76) | (107.48) | 65.51[C] | (128.17) | 90.17[B] |

[1]Feeding period was 6 weeks. Time of drawing the blood was 0.009 hr.
[2]Data expressed as means ± SD; n = 6 samples of 3 swine per group; TRF = Tocotrienol-Rich-Fraction.
[3]Percentages of increases or decreases in respect to baseline value.
[A–C]Values not sharing a common superscript letter are different at $P < 0.01$.

TABLE XV

HDL:LDL CHOLESTEROL CONCENTRATION IN SERUM (mg/100 ml)[2]

| NUTRITIONAL STATE[1] | Experimental Diets Feeding Period | | | Percentage of Control Activity | Control Diet Feeding Period | Percentage of Control Activity |
|---|---|---|---|---|---|---|
| | 0-Time | 21 days | 42 days | | 70 days | |
| Normolipemic Swine | 1:4.47 | 1:4.54 | 1:3.90 | | 1:3.89 | |
| 1) Control Diet (CD) | (100.00)[3] | (101.57)[3] | (87.25)[3] | — | (87.02)[3] | — |
| Hypercholesterolemic | 1:8.02 | 1:8.38 | 1:11.19 | | 1:8.72 | |
| Swine | | | | | | |
| 2) Control Diet (CD) | (100.00) | (104.49) | (139.53) | 100.00[A] | | 100.00[A] |
| 3) CD + TRF RD-oil; | 1:7.59 | 1:7.44 | 1:7.89 | | 1:8.85 | |
| 50 ppm | (100.00) | (98.02) | (103.95) | 70.51[B] | | 101.41[A] |
| 4) CD + γ$_3$; 50 ppm | 1:8.16 | 1:7.33 | 1:6.79 | | 1:7.37 | |
| | (100.00) | (89.83) | (82.84) | 60.58[C] | | 84.52[B] |
| 5) CD + P-21-T$_3$; 50 ppm | 1:7.93 | 1:7.40 | 1:6.47 | | 1:7.31 | |
| | (100.00) | (93.32) | (81.59) | 57.82[C] | | 83.83[B] |
| 6) CD + P-25-T$_3$; 50 ppm | 1:8.34 | 1:7.44 | 1:6.22 | | 1:7.16 | |
| | (100.00) | (89.20) | (74.58) | 55.59[D] | | 82.06[B] |

[1]Feeding period was 6 weeks. Time of drawing the blood was 0.009 hr. TRF = Tocotrienol-Rich-Fraction.
[2]Data expressed as means ± SD; n = 6 samples of 3 swine per group.
[3]Percentages of increases or decreases in respect to baseline value.
[A–D]Values not sharing a common superscript letter are different at $P < 0.01$.

All tocotrienols tested caused the levels of total serum cholesterol and LDL-cholesterol to decrease by about 25% and 10%, respectively. In addition, the HDL-/LDL-cholesterol ratio was reduced by about 20% with all three tocotrienols tested. These reductions were all time dependent. Moreover, the reductions observed after 42 days persisted over the 10 weeks following termination of tocotrienol feeding. This result suggests that the tocotrienols remain in the blood stream over extended periods of time. While not wishing to be bound by theory, we believe that the tocotrienols might be transported in association with the LDL- and HDL-lipoproteins. Alternatively, the tocotrienols may also bind to other proteins.

EXAMPLE 17

This example was conducted to measure the serum levels of apolipoprotein (a)$_1$, apolipoprotein B, triglycerides, glucose, insulin and glucagon and the plasma levels of thromboxane B$_2$ and platelet factor 4 in the swine described in Example 15.

The samples were prepared as described in Example 12.

The results of these studies are displayed in Tables XVI and XVII. Percentages of increases and decreases are shown in parentheses.

TABLE XVI

| | Concentration in Serum (mg/100 ml) | | |
|---|---|---|---|
| NUTRITIONAL STATE[1] | Apo A$_1$ | Apo B | Triglycerides |
| Hypercholesteralemic Swine | 25.69 ± 1.19 (100.00)$^A$ | 147.77 ± 1.50 (100.00)$^A$ | 76.56 ± 1.22 (100.00)$^A$ |
| 1) Control Diet (CD) | | | |
| 2) CD + TRF RB-oil; 50 ppm | 26.26 ± 1.07 (102.22)$^A$ | 118.39 ± 1.50 (80.12)$^A$ | 66.67 ± 1.39 (106.15)$^B$ |
| 3) CD + γ-T$_3$; 50 ppm | 26.22 ± 1.11 (102.06)$^A$ | 114.29 ± 1.79 (77.34)$^C$ | 61.78 ± 1.09 (80.69)$^C$ |
| 4) CD + P-21-T$_3$; 50 ppm | 26.72 ± 1.14 (104.01)$^A$ | 111.78 ± 1.80 (75.64)$^C$ | 64.44 ± 1.29 (84.17)$^B$ |
| 5) CD + P-25-T$_3$; 50 ppm | 26.73 ± 1.22 (104.05)$^A$ | 106.63 ± 1.72 (72.16)$^D$ | 62.00 ± 1.19 (80.98)$^C$ |

[1]Feeding period was 6 weeks. Time of drawing the blood was 0.009 hr.
[2]Data expressed as means ± SD; n = 6 samples of 3 swine per group; TRF = Tocotrienol-Rich-Fraction.
[3]Percentages of increases or decreases in respect to baseline value.
$^{A-D}$Values not sharing a common superscript letter are different at $P < 0.01$.

TABLE XVII

| NUTRITIONAL STATE[1] | Glucose (mg/100 ml) | Insulin (μG/ML) | Glucagon (pg/ml) | Thromboxane B$_2$ (pg/100 ml) | Platelet Factor 4 (mg/100 ml) |
|---|---|---|---|---|---|
| Hypercholesterolemic Swine | 95.99 ± 1.37$^A$ (100.00) | 10.50 ± 0.12$^A$ (100.00) | 330.41 ± 14.08$^A$ (100.00) | 75.93 ± 1.45$^A$ (100.00) | 24.12 ± 1.75$^A$ (100.00) |
| 1) Control Diet (CD) | | | | | |
| 2) CD + TRF RB-oil; 50 ppm | 74.45 ± 1.03$^B$ (77.56) | 23.10 ± 1.08$^B$ (112.68) | 295.36 ± 10.45$^B$ (89.39) | 64.55 ± 1.28B (95.23) | 20.32 ± 1.70$^B$ (84.30) |
| 3) CD +γ-T$_3$; 50 ppm | 74.40 ± 1.12$^B$ (77.51) | 21.21 ± 0.89$^B$ (103.46) | 285.41 ± 13.88$^B$ (86.38) | 62.54 ± 1.39$^B$ (92.25) | 20.65 ± 1.15$^B$ (85.28) |
| 4) CD + P-21-T3; 50 ppm | 72.63 ± 1.58$^B$ (75.66) | 21.45 ± 0.87$^B$ (104.63) | 278.36 ± 16.42$^B$ (84.25) | 60.48 ± 1.46$^B$ (87.66) | 19.85 ± 1.27$^{B,C}$ (82.59) |
| 5) CD + P-25-T3; 50 ppm | 71.89 ± 1.89$^B$ (74.89) | 20.89 ± 1.79$^B$ (101.90) | 274.41 ± 12.32$^B$ (83.05) | 57.03 ± 1.95$^{B,C}$ (83.02) | 19.15 ± 1.45$^{B,C}$ (79.36) |

[1]Corn-soybean meal control diet or experimental diets were fed to 5-month-old swine for 42 days. Then all groups were fasted for 40 hrs. and refed for 48 days. The time of sacrificing was 9:00 a.m. All tissues were kept an ice. TRF = Tocotrienol-Rich-Fraction.
[2]Data expressed as means ± SD; n = 6 samples of 3 swine per group;
[3]Percentages of increases or decreases in respect to baseline value.
$^{A-C}$Values not sharing a common superscript letter are different at $P < 0.01$.

These results show that all the tocotrienols tested reduced levels of apolipoprotein B, triglycerides, glucose, glucagon and platelet factor 4 by about 30%, 20%, 25%, 17% and 21%, respectively. The tocotrienols did not substantially affect the levels of apolipoprotein (a)$_1$ and insulin.

EXAMPLE 18

We next determined the effect of tocotrienols on the total cholesterol, triglyceride and glucose concentrations in various tissues of hypercholesterolemic swine.

The samples were prepared as described in Example 12.

The results of these studies are displayed in Tables XVIII–XX. Percentages of increases and decreases are shown in parentheses.

TABLE XVIII

TOTAL CHOLESTEROL CONCENTRATION (mg/100 gm)[2]

| NUTRITIONAL STATE[1] | Liver | Intestine | Lung | Heart | Loin Muscle | Adipose Tissue | Ham Muscle |
|---|---|---|---|---|---|---|---|
| Normalipemic Swine | 151.59 ± 6.22 | 175.10 ± 6.61 | 76.45 ± 7.19 | 60.50 ± 3.49 | 97.89 ± 4.14 | 92.86 ± 5.51 | 86.09 ± 2.57 |
| 1) Control Diet (CD) | | | | | | | |

TABLE XVIII-continued

TOTAL CHOLESTEROL CONCENTRATION (mg/100 gm)[2]

| NUTRITIONAL STATE[1] | Liver | Intestine | Lung | Heart | Loin Muscle | Adipose Tissue | Ham Muscle |
|---|---|---|---|---|---|---|---|
| Hypercholesterolemic Swine 2) Control Diet (CD) | 201.59 ± 5.68[A] (100.00) | 215.49 ± 5.78[A] (100.00) | 101.74 ± 4.34[A] (100.00) | 64.51 ± 9.61[A] (100.00) | 119.62 ± 3.89[A] (100.00) | 109.40 ± 4.00[A] (100.00) | 100.00 ± 3.73[A] (100.00) |
| 3) CD + TRF RB-oil; 50 ppm | 172.22 ± 4.19[B] (85.43) | 198.63 ± 3.75[B] (92.18) | 91.12 ± 2.28[B] (89.56) | 58.78 ± 1.87[B] (91.12) | 112.69 ± 2.63[B] (94.21) | 102.25 ± 1.94[A] (93.46) | 93.05 ± 3.44[B] (93.05) |
| 4) CD + γ-T$_3$; 50 ppm | 149.20 ± 3.83[C] (74.01) | 187.06 ± 4.27[C] (86.81) | 83.79 ± 3.24[C] (82.36) | 56.68 ± 1.91[B] (87.86) | 103.48 ± 2.39[C] (86.51) | 94.55 ± 3.03[C] (86.43) | 85.15 ± 2.24[C] (85.15) |
| 5) CD + P-21-T$_3$ 50 ppm | 136.70 ± 4.55[D] (67.81) | 180.59 ± 3.03[C,D] (83.80) | 75.68 ± 4.14[D] (74.39) | 53.63 ± 2.01[C] (83.13) | 100.58 ± 1.71[C] (84.09) | 89.85 ± 2.17[B] (82.13) | 79.51 ± 3.75[C] (79.51) |
| 6) CD + P-25-T$_3$; 50 ppm | 125.21 ± 4.30[E] (62.11) | 176.67 ± 5.41[E] (81.98) | 68.5 ± 5.32[D] (66.98) | 51.53 ± 2.20[C] (82.79) | 99.04 ± 3.52[C] (81.85) | 89.54 ± 1.98[B] (81.85) | 69.17 ± 3.88[D] (69.17) |

[1]Corn-soybean meal control diet or experimental diets were fed to 5-month-old swine for 42 days. Then all groups were fasted for 40 hrs. and refed for 48 days. The time of sacrificing was 9:00 a.m. All tissues were kept an ice. TRF = Tocotrienol-Rich-Fraction.
[2]Data expressed as means ± SD; n = 6 samples of 3 swine per group;
[A–E]Values not sharing a common superscript letter are different at $P < 0.01$.

TABLE XIX

TOTAL TRIGLYCERIDES CONCENTRATION (mg/100 gm)[2]

| NUTRITIONAL STATE[1] | Liver | Intestine | Lung | Heart | Loin Muscle | Adipose Tissue | Ham Muscle |
|---|---|---|---|---|---|---|---|
| Normalipemic Swine 1) Control Diet (CD) | 388.68 ± 5.80 | 300.24 ± 5.63 | 163.53 ± 3.57 | 130.51 ± 3.59 | 207.55 ± 5.50 | 294.43 ± 4.99 | 187.50 ± 3.68 |
| Hypercholesterolemic Swine 2) Control Diet (CD) | 429.36 ± 5.02[A] (100.00) | 357.63 ± 4.48[A] (100.00) | 171.96 ± 4.04[A] (100.00) | 144.22 ± 3.29[A] (100.00) | 219.68 ± 5.19[A] (100.00) | 435.68 ± 3.79[A] (100.00) | 165.83 ± 4.05[A] (100.00) |
| 3) CD + TRF RB-oil; 50 ppm | 409.80 ± 6.48[B] (95.44) | 355.93 ± 3.07[A] (99.52) | 166.66 ± 2.49[A] (96.92) | 140.71 ± 3.35[A] (97.57) | 212.27 ± 7.09[B] (96.63) | 421.42 ± 3.45[B] (96.73) | 184.99 ± 2.40[A] (99.55) |
| 4) CD + γ-T$_3$; 50 ppm | 397.51 ± 3.88[C] (92.58) | 351.33 ± 2.80[A,B] (98.24) | 167.18 ± 2.86[A] (97.22) | 142.72 ± 1.28[A] (98.96) | 201.65 ± 2.01[C] (91.79) | 391.58 ± 7.59[C] (89.88) | 181.99 ± 1.67[A] (97.93) |
| 5) CD + P-21-T$_3$; 50 ppm | 386.25 ± 5.10[D] (89.96) | 347.75 ± 4.74[B] (97.24) | 165.47 ± 2.26[A] (96.22) | 142.38 ± 1.73[A] (98.72) | 194.75 ± 1.72[D] (88.65) | 282.82 ± 6.86[C] (64.91) | 182.16 ± 1.28[A] (98.03) |
| 6) CD + P-25-T$_3$; 50 ppm | 384.00 ± 2.98[D] (89.44) | 345.37 ± 3.97[B] (96.57) | 163.42 ± 2.46[A] (95.03) | 140.51 ± 0.99[A] (97.43) | 189.18 ± 1.68[E] (86.12) | 259.62 ± 7.47[D] (59.59) | 182.98 ± 1.76[A] (98.44) |

[1]Corn-soybean meal control diet or experimental diets were fed to 5-month-old swine for 42 days. Then all groups were fasted for 40 hrs. and refed for 48 days. The time of sacrificing was 9:00 a.m. All tissues were kept an ice. TRF = Tocotrienol-Rich-Fraction.
[2]Data expressed as means ± SD; n = 6 samples of 3 swine per group;
[A–D]Values not sharing a common superscript letter are different at $P < 0.01$.
Percentages of control activity are given in parentheses.

TABLE XX

TOTAL GLUCOSE CONCENTRATION (mg/100 gm)[2]

| NUTRITIONAL STATE[1] | Liver | Intestine | Lung | Heart | Loin Muscle | Adipose Tissue | Ham Muscle |
|---|---|---|---|---|---|---|---|
| Normalipemic Swine 1) Control Diet (CD) | 361.05 ± 7.79 | 66.86 ± 5.81 | 61.35 ± 6.45 | 42.86 ± 1.91 | 65.79 ± 2.57 | 21.85 ± 5.01 | 53.82 ± 2.60 |
| Hypercholesterolemic Swine 2) Control Diet (CD) | 405.23 ± 7.68[A] (100.00) | 71.97 ± 2.97[A] (100.00) | 66.93 ± 4.40[A] (100.00) | 49.25 ± 2.91[A] (100.00) | 71.24 ± 1.26[A] (100.00) | 18.34 ± 2.60[A] (100.00) | 53.82 ± 2.60[A] (100.00) |

TABLE XX-continued

TOTAL GLUCOSE CONCENTRATION (mg/100 gm)[2]

| NUTRITIONAL STATE[1] | Liver | Intestine | Lung | Heart | Loin Muscle | Adipose Tissue | Ham Muscle |
|---|---|---|---|---|---|---|---|
| 3) CD + TRF RB-oil; 50 ppm | 395.54 ± 3.82[A] (97.61) | 64.02 ± 2.80[B] (88.95) | 66.16 ± 3.82[A] (98.85) | 46.80 ± 2.50[A] (95.03) | 64.48 ± 2.70[B] (90.51) | 17.04 ± 1.35[A,B] (92.01) | 52.10 ± 1.90[A] (96.80) |
| 4) CD + γ-T$_3$; 50 ppm | 383.68 ± 3.37[B] (94.53) | 62.50 ± 2.36[B,C] (86.84) | 63.08 ± 3.38[A,B] (94.25) | 46.81 ± 3.21[A] (95.05) | 60.30 ± 1.95[B] (84.64) | 15.93 ± 1.77[A,B] (86.86) | 52.10 ± 1.69[A] (96.80) |
| 5) CD + P-21-T$_3$; 50 ppm | 374.22 ± 3.19[C] (92.35) | 62.50 ± 2.80[B,C] (86.84) | 61.92 ± 2.63[B] (92.51) | 44.17 ± 3.55[A] (89.69) | 55.45 ± 1.88[C] (77.84) | 16.67 ± 1.96[A,B] (90.89) | 54.01 ± 1.73[A] (100.35) |
| 6) CD + P-25-T$_3$; 50 ppm | 362.99 ± 4.31[D] (89.58) | 56.06 ± 4.06[C] (77.89) | 60.96 ± 5.41[B] (91.08) | 45.49 ± 2.78[A] (92.37) | 53.01 ± 1.30[C] (74.41) | 14.96 ± 1.26[B] (81.57) | 53.05 ± 2.61[A] (98.57) |

[1]Corn-soybean meal control diet or experimental diets were fed to 5-month-old swine for 42 days. Then all groups were fasted for 40 hrs. and refed for 48 days. The time of sacrificing was 9:00 a.m. All tissues were kept an ice. TRF = Tocotrienol-Rich-Fraction.
[2]Data expressed as means ± SD; n = 6 samples of 3 swine per group;
[3]Percentages of increases or decreases in respect to baseline value.
[A–C]Values not sharing a common superscript letter are different at P < 0.01.

Decreases in total serum cholesterol were found in the each of the tissues tested. Most notably, total cholesterol concentration was reduced by 37% and 30% with $P_{25}$ in the liver and ham muscle, respectively. Total triglyceride and glucose concentrations were less affected.

EXAMPLE 19

We next measured the effects of different tocotrienols of rice bran oil on fatty acid compositions in various tissue of hypercholesterolemic swine.

The levels of fatty acids, measured as their esters, were estimated using the method described in K. Hirai et al., "Effects of Dietary Fats and Phytosterol on Serum Fatty Acid Composition and Lipoprotein Cholesterol in Rats", *J. Nutr. Sci. Vitaminol.*, 30, pp. 101–112 (1984), except that 1 g of each tissue was mixed with 2 ml of saline solution, the homogenized 30 sec by polytron. Following homogenization, the sample was extracted with 8 ml of hexane by shaking for 20 min., then centrifuging for 10 min. at 2000 rpm. The hexane layer was dried at 40° C. and the residue treated with 0.5 ml diazomethane to yield the fatty acid esters.

The identification of each fatty acid ester was established by comparison against a standard mixture of fatty acid esters (obtained from Sigma Chemical Co.).

The results, as displayed in FIGS. 1–4, demonstrate that the tocotrienols tested were able to lower the total fatty acid concentration in every tissue tested. The most impressive declines were seen in the heart (76%), the loin (81%) and the ham muscle (66%). The greatest reductions were seen in levels of arachidonic acid. This decrease may be due to an increase in the corticosterone levels. Such an increase would inhibit the activity of phospholipase $A_2$, which would in turn decrease the arachidonic acid metabolites. The overall fatty acid reduction is also important because it points towards an immunoregulatory role of these tocotrienols.

EXAMPLE 20

We next determined the effect of tocotrienols on immune function. The model for this study was 6-week old female white leghorn chickens. Each group of 12 chickens was fed an unsupplemented chicken diet or a control diet supplemented with 50 ppm of a tocotrienol or 100 ppm of a commercially available hypercholesterolemic agent (Geraniol or Lovastatin). The samples were prepared as described in Example 11. The chickens were fed over a period of 4 weeks, then the blood was drawn. The antibody response was determined by injecting the chickens i.p. with 0.5 ml of a 5% suspension of sheep red blood cells (RBCs) in PBS (v/v) which were previously washed three times. Total antibody titers to the RBCs were determined using 50 μg of serum and the microhemagglutination technique described in Witlin, "Detection of Antibodies by Microtitration Techniques", *Mycopth. Mycol. Appl.*, 33, pp. 241–257 (1967). Relative IgG levels were determined by using 2-mercaptoethanol preincubation for 30 min. The relative IgM levels were calculated by subtracting the IgG antibody levels from total antibody levels. All antibody levels are expressed as the log base 2 of the highest titer that was needed to hemagglutinate an equal volume of 0.5% RBC suspension. The results of this example are displayed below in Table XXI.

TABLE XXI

Antibody titers in Serum (Log 2)

| Nutritional State[1] | Total Ab titers | IgG | IgM |
|---|---|---|---|
| 1) Control Group (CD) | 6.30 ± 2.99[A] | 1.40 ± 0.55[A] | 5.67 ± 0.09[A] |
| 2) CD + TRF-RBO 50 ppm | 8.75 ± 1.66[A] | 1.50 ± 0.54[A] | 7.75 ± 1.55[A] |
| 3) CD + α-T$_3$ 50 ppm | 7.10 ± 1.51[A] | 1.00 ± 0.00[A] | 6.60 ± 1.24[A] |
| 4) CD + γ-T$_3$ 50 ppm | 6.60 ± 1.51[A] | 1.28 ± 0.49[A] | 5.83 ± 1.53[A] |
| 5) CD + δ-T$_3$ 50 ppm | 8.67 ± 1.78[A] | 1.00 ± 0.00[A] | 8.25 ± 1.96[A] |
| 6) CD + P-21-T$_3$ 50 ppm | 8.67 ± 1.92[A] | 1.50 ± 1.18[A] | 7.17 ± 2.04[A] |
| 7) CD + P-25-T$_3$ 50 ppm | 10.30 ± 1.16[B] | 2.43 ± 1.40[A] | 8.92 ± 2.61[A] |
| 8) CD + Geranial | 5.60 ± 2.11[A] | 1.00 ± 0.00[A] | 5.42 ± 2.02[A] |
| 9) Lovastatin 100 ppm | 6.33 ± 1.44[A] | 1.00 ± 0.00[A] | 5.90 ± 1.68[A] |
| 10) Geraniol + Lovastatin 50 ppm + 50 ppm | 7.17 ± 2.04[A] | 1.00 ± 0.00[A] | 6.83 ± 1.99[A] |

[1]Feeding period was 4 weeks. Time of drawing the blood as 0800 hr. Data expressed as means + SD; n = 12 birds per group.
[A–B]Values not sharing a common superscript letter are different at P < 0.01.

Every tocotrienol, most notably $P_{25}$, increased the total antibody titer and the IgM titer as compared to the control. Slight increases were also observed in the IgG levels.

EXAMPLE 21

We determined the effect of a known tocotrienol, γ-$T_3$, on the release of superoxide in human peripheral blood neutrophils. Neutrophils are an extracellular source of oxygen free radicals. Once activated, these neutrophils can attach to endothelial tissue where they release a potent toxin, superoxide. Superoxide amplifies the inflammatory response and impairs local circulation of the blood.

The neutrophils we tested were isolated by density centrifugation on Ficoll-Hypaque gradients using conventional methods (see E. Serbinova et al., "Free Radical Recycling and Intramembrane Mobility in the Antioxidant Properties of α-Tocopherol and α-Tocotrienol", *Free Rad. Bio. and Med.*, 10, pp. 263–75 (1991)). The neutrophils were then placed in a 96-well plate. γ-$T_3$ and phorbol myrstate acetate were added to the wells at the same time. The secretion of superoxide anion was measured as the superoxide dismutase-inhibitable reduction of ferricytochrome C.

The results of this study are displayed in FIG. 5.

The amount of superoxide released was reduced from 19.7 nmole (for $5\times10^5$ cells/hour) in the control to 8.0 and 0 nmole at γ-$T_3$ concentrations of $10^{-6}$ and $10^{-5}$, respectively.

While we have described a number of embodiments of this invention, it is apparent that our basic constructions may be altered to provide other embodiments which utilize the processes and products of this invention. Therefore, it will be appreciated that the scope of this invention is to be defined by the appended claims, rather than be the specific embodiments which have been presented by way of example.

What is claimed is:

1. A method for treating an inflammatory condition in a subject in need thereof comprising administering to said subject a composition comprising an effective amount of a tocotrienol or a mixture of tocotrienols.

2. The method according to claim 1, wherein the tocotrienol is selected from the group consisting of α-tocotrienol, β-tocotrienol, γ-tocotrienol, δ-tocotrienol, a mixture of said tocotrienols or a mixture of tocotrienols and tocopherols (a TRF).

3. The method according to claim 1, wherein the tocotrienol has the following formula:

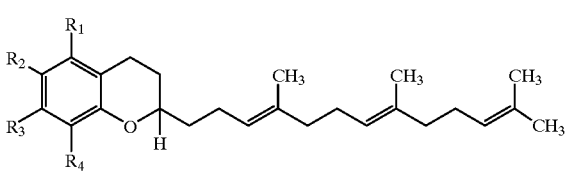

wherein $R_1$ and $R_3$ are independently selected from the group consisting of H, halogen, OH, $OCH_3$ and $C_1$–$C_6$ branched or unbranched alkyl;

$R_2$ is selected from the group consisting of OH, $NHR_5$, $CO_2Y$, $C(R_5)_2CO_2Y$, and $C_1$–$C_6$ branched or unbranched alkyl substituted with a group selected from the group consisting of OH, $NHR_5$, $CO_2Y$ or $C(R_5)_2CO_2Y$;

$R_4$ is H, halogen, OH, $CH_2OH$, $CH_3$, $OCH_3$ or $COCH_3$;

$R_5$ is selected from the group consisting of H and $C_1$–$C_6$ branched or unbranched alkyl; and Y is H, $C_1$–$C_{18}$ branched or unbranched alkyl or the salt of an acid.

4. The method according to claim 3, wherein the tocotrienol has the following formula:

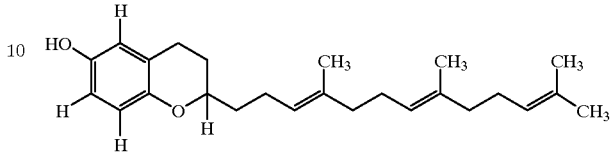

5. The method according to claim 1, wherein the tocotrienol has the following formula:

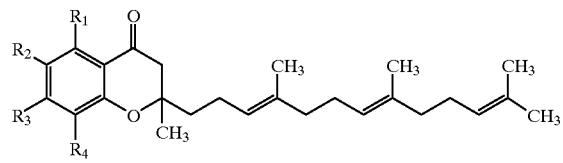

wherein $R_1$ and $R_3$ are independently selected from the group consisting of H, halogen, OH, $OCH_3$ and $C_1$–$C_6$ branched or unbranched alkyl;

$R_2$ is selected from the group consisting of OH, $NHR_5$, $CO_2Y$, $C(R_5)_2CO_2Y$, and $C_1$–$C_6$ branched or unbranched alkyl substituted with a group selected from the group consisting of OH, $NHR_5$, $CO_2Y$ or $C(R_5)_2CO_2Y$;

$R_4$ is H, halogen, OH, $CH_2OH$, $CH_3$, $OCH_3$ or $COCH_3$;

$R_5$ is selected from the group consisting of H and $C_1$–$C_6$ branched or unbranched alkyl; and Y is H, $C_1$–$C_{18}$ branched or unbranched alkyl or the salt of an acid.

6. The method according to claim 5, wherein the tocotrienol has the following formula:

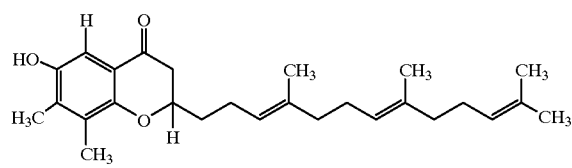

7. The method according to any one of claims 1–6, wherein said composition further comprises α-tocopherol, β-tocopherol, δ-tocopherol, γ-tocopherol or a combination thereof.

8. The method according to claims 1–6, wherein the inflammatory condition is selected from the group consisting of essential hypertension, hypertension of congestive heart failure, renal dysfunction caused by reduced myocardial output, endotoxemia, chronic liver disease, hypertension, pulmonary inflammation in asthma, bronchitic phenumonia acute lung injury, rheumatic diseases, inflammatory bowel disease and irritable bowel disease.

9. The method according to claim 8, wherein the inflammatory condition is selected from rheumatoid diseases and pain.

10. The method according to claims 1–6, wherein said composition is a pharmaceutical composition.

11. The method according to claims 1–6, wherein said composition is a foodstuff.

12. The method according to claims 1–6, wherein said composition is a dietary supplement.

13. A method for inhibiting production of superoxide and the consequences of superoxide production comprising administering to a human or animal a therapeutically effective amount of a tocotrienol or a TRF.

14. The method of claim 13, wherein the tocotrienol is selected from the group consisting of α-tocotrienol, β-tocotrienol, γ-tocotrienol, δ-tocotrienol, P18 tocotrienol and P25 tocotrienol.

* * * * *